(12) United States Patent
Tanaka

(10) Patent No.: US 9,139,810 B2
(45) Date of Patent: Sep. 22, 2015

(54) METHOD FOR CULTURING MICROORGANISMS TO INCORPORATE A SUBSTITUE ELEMENT

(75) Inventor: Yoshitake Tanaka, Tokyo (JP)

(73) Assignee: PARA MICROBIOS LABORATORIES, Tokyo (JP)

( * ) Notice: Subject to any disclaimer, the term of this patent is extended or adjusted under 35 U.S.C. 154(b) by 0 days.

(21) Appl. No.: 13/977,148

(22) PCT Filed: Sep. 5, 2011

(86) PCT No.: PCT/JP2011/070152
§ 371 (c)(1),
(2), (4) Date: Jun. 28, 2013

(87) PCT Pub. No.: WO2012/090554
PCT Pub. Date: Jul. 5, 2012

(65) Prior Publication Data
US 2013/0288340 A1    Oct. 31, 2013

(30) Foreign Application Priority Data

Dec. 28, 2010  (JP) .................................. 2010-294074

(51) Int. Cl.
| | |
|---|---|
| C12N 1/38 | (2006.01) |
| C12N 1/36 | (2006.01) |
| A23L 1/30 | (2006.01) |
| C12N 1/14 | (2006.01) |
| C12N 1/20 | (2006.01) |
| C12N 1/16 | (2006.01) |
| C12N 1/18 | (2006.01) |

(52) U.S. Cl.
CPC ................ C12N 1/36 (2013.01); A23L 1/3014 (2013.01); C12N 1/14 (2013.01); C12N 1/16 (2013.01); C12N 1/18 (2013.01); C12N 1/20 (2013.01); C12N 1/38 (2013.01)

(58) Field of Classification Search
USPC .................................................. 435/245, 30
See application file for complete search history.

(56) References Cited

U.S. PATENT DOCUMENTS

| | | | |
|---|---|---|---|
| 5,520,811 A | 5/1996 | Dick et al. | |
| 5,792,646 A | 8/1998 | Sohn et al. | |
| 6,368,643 B1 * | 4/2002 | Fan et al. | 426/62 |

FOREIGN PATENT DOCUMENTS

JP            2737636         1/1998

OTHER PUBLICATIONS

Knodle R. et al. From Phosphorus to Arsenic . . . Biomolecules 2(2)282-287, 2012.*
Erb, T. et al. GFAJ-1 Is an Arsenate Resistant Phosphate Dependent Organism. Science 337(6093)467-470, Jul. 27, 2012.*
Crans et al., "The chemistry and biochemistry of Vanadium and the biological activities exerted by vanadium compounds," Chem. Rev., 2004, vol. 104, pp. 849-902.
Okamoto et al., "Intermediate structure and mechanism of molybdenum hydroxylase reaction," Biochemistry, 2008, vol. 80, No. 6, pp. 531-539 (Partial English translation provided).
Zehr et al., "Nitrogenase gene diversity and microbial community structure: a cross-system comparison," Environ. Microbiol., 2003, vol. 5, No. 7, pp. 539-554.
Rehder, "Vanadum nitrogenase," Inorg Biochem, 2000, vol. 80, pp. 133-136.
Seefeldt et al., "Mechanism of Mo-dependent nitrogenase," Annu Rev Biochem, 2009, vol. 78, pp. 701-722.
Rubio et al., "Biosynthesis of the iron-molybdenum cofactor of nitrogenase," Annu, Rev. Microbiot., 2008, vol. 62, pp. 93-111.
Hecky et al., "The amino acid and sugar composition of diatom-cell-walls," Marine Biology, 1973, vol. 19, pp. 323-331.
Sabourin et al., "Biodegradation of dimethylsilanediol in soils," Appl. Environ. Microbiol., 1996, vol. 62, No. 12, pp. 4352-4360.
Cabello et al., "Effect of an arbuscular mycorrhizal fungus, Glomus mosseae, and a rock-phosphate-solubilizing fungus, *Penicillium thomii*, on *Mentha piperita* growth in a soilless medium," J. Basic Microbiot., 2005, vol. 45, No. 3, pp. 182-189.
Ramadan et al., "Incorporation of tellurium into amino acids and proteins in a tellurium-tolerant fungi," Biol Trace Elem Res., 1989, vol. 20, No. 3, pp. 225-232.
Wolfe-Simon et al., "A bacterium that can grow by using arsenic instead of phosphorus," Science, Dec. 2, 2010, (published Online), hitp://www.sciencemag.org/content/early/2010/12/01/science.
1197258 (full text), and http://www.sciencemag.org/content/suppl/2010/12/01/science.1197258.DC1/Wolfe-Simon-SOM.pdf (supporting online material), retrieved from the Internet [retrieved on Sep. 26, 2011].
Budisa et al., High-level biosynthetic substitution of methionine in proteins by its analogs 2-aminohexanoic acid, selenomehionine, telluromethionine, and ehionine in *Escherichia coli.*, Eur. J. Biochem., 1995, vol. 230 pp. 788-796.
Muller et al., "The formation of diselenide bridges in proteins by incorporation of selenocysteine residues: Biosynthesis and characterization of $(Se)_2$-Thioredoxin.," Biochemistry, 1994, vol. 33, p. 3404-3412.
Lane et al., "A biological function for cadmium in marine diatoms," Proc. Natl. Acad. Sci. USA, 2000, vol. 97, No. 9, pp. 4627-4631.
Rehder, "Vanadium nitrogenase," Journal of Inorganic Biochemistry, 2000, No. 80, pp. 133-136.
Hille, "Molybdenum and tungsten in biology," Trends in Biochemical Sciences, 2002, vol. 22, No. 7, pp. 360-367.
Bertini et al., Bioinorganic Chemistry, Mill Valley: University Science Books, 1994 (93 pages total).

* cited by examiner

*Primary Examiner* — Ralph Gitomer
(74) *Attorney, Agent, or Firm* — Hamre, Schumann, Mueller & Larson, P.C.

(57) ABSTRACT

An object of the present invention is to provide a microorganism at the elemental composition level, and to provide a technique for providing such a microorganism. The present inventor has succeeded in causing a microorganism to efficiently contain a non-essential element by decreasing the content of an essential nutrient source for the microorganism, a C source, an N source, a P source, or an S source, and by adding an X compound containing the non-essential element as a constitutive element in a manner to make up for the decreased amount, and then culturing the microorganism.

17 Claims, 15 Drawing Sheets

METHOD FOR CULTURING MICROORGANISMS TO INCORPORATE A SUBSTITUE ELEMENT

This application is a National Stage application filed under Rule 371 based upon PCT/JP2011/070152 filed Sep. 5, 2011.

TECHNICAL FIELD

The present invention relates to a novel method for culturing a microorganism, a method for producing microbial cells that have a novel elemental composition, which comprises causing the microorganism to use a compound containing a substitute element substituting for an essential element through the use of the culture method, and the thus produced microorganism.

BACKGROUND ART

1. Introduction

When studied on the basis of morphological classification, microorganisms are of many types. However, when considered from the view point of essential elements that compose cells, microorganisms are of fewer types. There is a total of 11 kinds of major essential elements that compose microbial cells: 6 organic elements (C, N, P, S, O, and H); and 5 electrolytic elements (Na, K, Ca, Mg, and Cl) are most probably contained in all microorganisms. In addition to these essential elements, it is known that, from among 9 basic trace elements (V, Mo, Se, Mn, Fe, Co, Ni, Cu, and Zn), 2 elements (V and Mo) are contained in specific microbial species, while the remaining 7 elements are contained by almost all microorganisms. Moreover, any specific microbial species contains or does not contain at least one of 3 general trace elements (W, Si, and Sn).

2. Essential Element

Whether or not an element is essential for an organism can be revealed by a method that involves examining the amount of an element to be supplied and a biological reaction, which indicates whether the element is essential for the organism, for example. Specifically, by using the method and technique determination is made that an element is essential for an organism, when the supply of the element is gradually increased from null, then the resulting biological reactions appear within a dose range in as per the following order: no growth, weak growth or nutritional deficiency, accelerated growth, optimum growth, poor growth, presence of harmful symptoms, and impossibility in growth or death. Specifically, under a particular growth environment, for example, suppose that Zn within a low-concentration range has the effect of delaying mouse growth. Zn, when given in a concentration that is slightly higher than such concentration range, promotes the growth in an accelerated manner, but Zn in an even higher concentration has an inhibitory effect, then, Zn would be regarded as an essential element for mice. These results are considered to be nutritional evidence indicating that the relevant element is essential.

3. Non-Essential Elements Contained in General Microorganisms are Reported as Below.

3-1. (V, Mo)

The element vanadium (V) has been proven to be an essential element for rats and chicks (Non-patent Literature 1). It is also known that vanadium is present at a particularly high concentration in blood cells of sea squirts. However, the origin of "V" in sea squirts, the assimilation mechanism thereof, and the role thereof remain unclear. It is also known that molybdenum-containing hydroxylase is present in many biological species ranging from bacteria to humans (Non-patent Literature 2).

Higher plants do not have their own capacity for using nitrogen in the air. The supply of ammonia or a nitric acid group depends on the microbial capacity for fixing nitrogen. A nitrogenase enzyme that is responsible for a reaction that generates ammonia from nitrogen in air, which is an important stage of microbial nitrogen fixation, is a metal enzyme containing V or Mo. Hence, nitrogen-fixing microbial cells contain V or Mo (Non-patent Literature 3-6). Whether a microorganism contains V or Mo differs depending on microbial species.

Examples of nitrogen-fixing bacteria include a dozen species of anaerobic or aerobic heterotrophic bacteria (e.g., *Azotobacter* sp., *Clostridium* sp., *Desulfovibrio* sp., *Escherichia* sp., and *Klebsiella* sp.), root nodule bacteria, *Rhizobium* sp., a symbiont living with leguminous plants, photosynthetic bacteria, and about 40 species of blue-green algae. Among approximately so-called a hundred thousand species of microorganisms, the number of species of nitrogen-fixing bacteria is limited, but they are broadly distributed on earth. When these nitrogen-fixing bacteria are grown under nitrogen fixation conditions, V and Mo are essential elements, but are not essential elements when the nitrogen-fixing bacteria are grown under heterotrophic conditions.

Meanwhile, a haloperoxidase enzyme, by which a reaction is conducted to degrade C-halogen bonding among limited species of mushrooms and fungi, is a metal enzyme containing V.

3-2. (Si)

Among microorganisms in broad terms (including bacteria, yeast, filamentous fungi, basidiomycetes and algae, and Protozoa), a type of algae needs Si. Diatoms contain Si as a constituent of cell walls, and thus Si is essential (Non-patent Literature 7). Si is also found in some kinds of *Radiolarida*. However, the need of Si has not been proven for general microorganisms (bacteria, yeast, filamentous fungi, and basidiomycetes) other than algae and diatoms.

Moreover, several microorganisms have been tested for the capacity for metabolizing an organic silicon compound or an organic silicone. As a result, it has been found that relatively many filamentous fungi and bacteria metabolize such an organic silicic acid compound (Non-patent Literature 8). It has also been found that a strain of *Bacillus* sp. is capable of eluting a phosphate group from a phosphorus ore (Non-patent Literature 9). In this case, microbial cells contain Si. However, although microorganisms degrade and metabolize organic carbon portions, their assimilation of silicon has never been reported. It is rather assumed that inorganic silicon is finally generated.

3-3. (Ge)

Ge-containing yeast cells were prepared (Patent Literature 1). In this literature, yeast was caused to incorporate Ge in a nutrient-rich medium. The literature describes that the Ge compound was incidentally incorporated by yeast with low incorporation efficiency and does not describe that such incorporation can be achieved by other microorganisms.

3-4. (Te)

It has been reported that filamentous fungi having natural resistance to a Te compound were caused to incorporate Te. Although Te was used for the filamentous fungi of this literature under conditions of a limited amount of an S source, the aforementioned literature does not report that Te can be used as an S source, P source, N source, or C source substitute in wide-ranging general microorganisms.

3-5. (Metal Adsorption by Microorganism)

As a result of studies to cause microorganisms to adsorb hazardous metals including Cr, Cd, Hg, and Pb in order to eliminate these metals, it has been found that many microorganisms adsorb various metals, as reported in Patent Literature 2, for example. For example, it has been reported that Pb was bound to cell membranes or outer membrane polysaccharides, and that when incorporation of lead citrate was attempted, its citric acid portion was metabolized as a nutrient, but Pb was bound to and deposited on cell surface layers.

3-6. (Conclusion)

As described above, a few facts indicating that microorganisms incorporate non-essential elements have been reported. These facts are characterized as follows.

1. Subject non-essential elements include highly toxic elements and the number of types thereof are limited to few.
2. Microorganisms used herein are a small number of specific microorganisms. These microorganisms were newly isolated from nature as microorganisms capable of incorporating compounds that contain elements of interest, or were selected from many existing microorganisms. It has not been described about whether or not microorganisms other than these selected strains could incorporate the elements of interest.
3. A case, in which a method for culturing microorganisms is improved for the purpose of causing them to incorporate safe or low-toxic non-essential elements, has never been reported. It has also never been reported that a microorganism can be modified by mutation or the like to make it possible to efficiently incorporate such elements.

CITATION LIST

Patent Literature

Patent Literature 1: JP Patent No. 2737636
Patent Literature 2: U.S. Pat. No. 5,520,811

Non-patent Literature

Non-patent Literature 1: The chemistry and biochemistry of vanadium and the biological activities exerted by vanadium compounds. Crans D C, Smee J J, Gaidamauskas E, Yang L. Chem Rev. 2004 February; 104 (2): 849-902.
Non-patent Literature 2: Biochemistry, Vol. 80, No. 6, pp. 531-539, 2008
Non-patent Literature 3: Nitrogenase gene diversity and microbial community structure: a cross-system comparison. Zehr J P, Jenkins B D, Short S M, Steward G F. Environ. Microbiol. 2003 July; 5 (7): 539-54.
Non-patent Literature 4: Vanadium nitrogenase. Rehder D. J. Inorg Biochem. 2000 May 30; 80 (1-2): 133-6.
Non-patent Literature 5: Mechanism of Mo-dependent nitrogenase. Seefeldt L C, Hoffman B M, Dean D R. Annu Rev Biochem. 2009; 78:701-22.
Non-patent Literature 6: Biosynthesis of the iron-molybdenum cofactor of nitrogenase. Rubio L M, Ludden P W. Annu. Rev. Microbiol. 2008; 62: 93-111.
Non-patent Literature 7: Diatoms-from cell wall biogenesis to nanotechnology. R E Hecky et al., Marine Biol., 1973, 19, 323.
Non-patent Literature 8: Biodegradation of dimethylsilanediol in soils. Sabourin C L, Carpenter J C, Leib T K, Appl. Environ. Microbiol. 1996 December; 62 (12): 4352-60.
Non-patent Literature 9: Effect of an arbuscular mycorrhizal fungus, *Glomus mosseae*, and a rock-phosphate-solubilizing fungus, *Penicillium thomii*, on *Mentha piperita* growth in a soilless medium. Cabello M, Irrazabal G, Bucsinszky A M, Saparrat M, Schalamuk S. J Basic Microbiol. 2005; 45 (3): 182-9.
Non-patent Literature 10: Incorporation of tellurium into amino acids and proteins in tellurium-tolerant fungi. Ramadan S E, Razak A A, Ragab A M, el-Meleigy M. Biol Trace Elem Res. 1989; 20 (3): 225-32

SUMMARY OF THE INVENTION

Problem to be Solved by the Invention

Major substances such as DNA or proteins composing cells of microorganisms such as *Escherichia coli* are constructed with common basic substances as materials. Major constituent elements of microbial cells are almost common. Therefore, in a search for a novel microorganism, an attempt with a hope to discover a novel microorganism, which is new at the element level, has been limited, since the number of combinations of elemental compositions is limited to a relatively small number thereof. If a microorganism that contains a novel element unknown to be used by a microorganism, instead of one of 6 organic elements, can be created, this must be a novel microorganism at the level of elemental composition. Such a microorganism can also be considered as a novel microorganism when it is classified by morphological and chemical classification techniques.

Hence, objects of the present invention are to provide a microorganism which is novel at the level of elemental composition and to provide a technique for providing such a microorganism.

Another object of the present invention is not to simply provide a microorganism to which a compound containing an element that is not generally used by a microorganism is adhered or absorbed, but to provide: microbial cells containing element X (that has never been thought to be an essential element for microorganisms) as an essential element; and a technique therefor.

Means for Solving the Problem

In the Description of the present application, a nutrition source containing the element C may be referred to as a C source, a nutrition source containing the element N may be referred to as an N source, a nutrition source containing the element P may be referred to as a P source, and a nutrition source containing the element S may be referred to as an S source.

The present inventor has succeeded in causing a microorganism to efficiently contain a non-essential element by decreasing the content of a C source, an N source, a P source, or an S source that is an essential nutrient source for the microorganism, and then culturing the microorganism in a medium supplemented with an X-containing compound that contains non-essential element X as a constitutive element to make up for the aforementioned decreased content.

As microorganisms, existing microorganisms, microorganisms isolated from samples in the natural environments, and wild-type strains as well as mutant strains exhibiting poor permeability for a C source, an N source, a P source, or an S source compound, metabolism-deficient mutant strains, and the like can be used.

The present description encompasses the contents described in the description and/or drawings of JP Patent Application No. 2010-294074, based on which the present application claims priority.

Effects of the Invention

According to the present invention, an existing microorganism is cultured in a medium supplemented with an X-containing compound that contains element X (that has hitherto never been found in microbial cells) as a constitutive element under conditions where any one of nutrition sources including a C source, an N source, a P source, and an S source is limited, so that the microorganism grows depending on the X-containing compound and can be caused to efficiently incorporate the element X. Specific examples of element X include Sc, Y, La, Nd, Eu, Er, Ti, V, Nb, Mo, W, B, Si, Ge, Sn, As, Sb, and Te.

The content of the element X is increased in the cells of the present invention compared with control cells; that is, cells obtained in an optimum medium containing a C source, an N source, a P source, an S source, and other nutrients in rich and appropriate amounts.

When the microbial cells of the present invention are caused to incorporate V or Mo, for example, the resulting content is 100 ppm or higher. Specifically, this is much higher than the 1 ppm level that is the content of V or Mo in nitrogen-fixing bacteria under natural weathering conditions.

BRIEF DESCRIPTION OF THE DRAWINGS

FIG. 2 further shows the results of examining the effects of subculture; that is, adaptation culture started at the end of the culture in a medium of the same composition.

EMBODIMENTS FOR CARRYING OUT THE INVENTION

Figure 1:
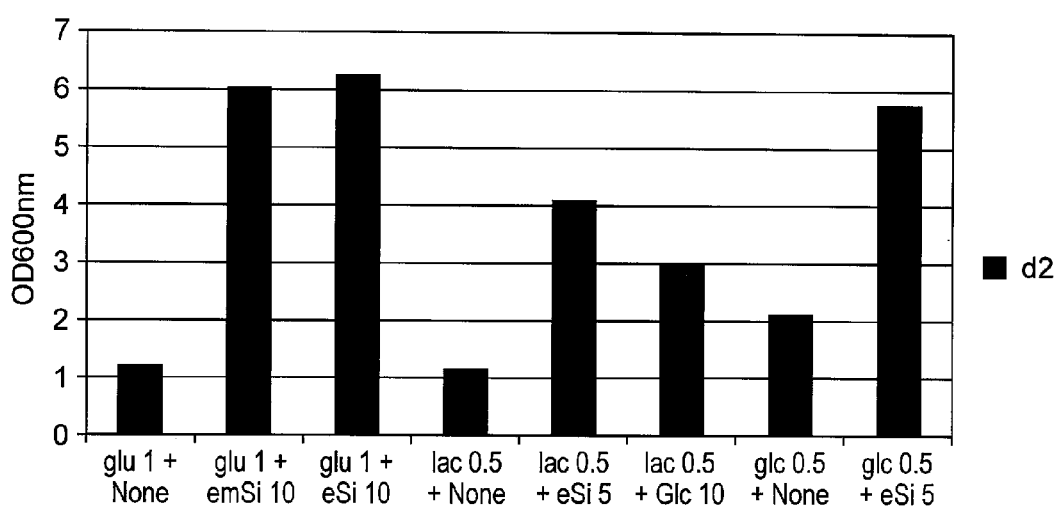
FIG. 1 shows the results of examining the growth of 3 strains of bacteria and fungi in C source-deficient media each supplemented with a limited amount of a C source (denoted as "αC") and an organic silicon compound as a C source substitute compound (denoted as "X").

1. Introduction 1-1. Elements Constituting Living Organism

It has been revealed that *Escherichia coli* cells comprise several structures including cell walls, cytoplasm membranes, cytoplasmic solutions, ribosomes, nuclei, and flagella as observed under a microscope. These structures are constructed by combining major substances (macromolecular compounds) such as DNA, proteins, polysaccharides, and lipids. These major substances are composed of a group of a small number of low-molecular-weight substances referred to as "basic substances for life" as building units parts. The term "basic substances for life" refers to 5 kind of nucleobase, 10 or more kind of sugars, 20 or more kind of amino acid, and 10 or more kind of fatty acid, for example. Specifically, a major substance, DNA is comprised of nucleobases (5 kinds of sugars), (2 types), and phosphoric acid. Another major substance, protein, is comprised of basically a straight linkage of 100 to 1,000 amino acids (20 kinds), wherein saccharides may be bound to some sites of the amino acid chains. Another major substance, polysaccharide, is comprised of sugars (10 or more kinds) that are linked in a straight or a branched chain linkage form, to which a phosphate group or a sulfate group or a fatty acid may be bound. A lipid is a compound in which glycerin and various fatty acids (10 or more kinds) are combined, bound, to which a polysaccharide, a phosphate group, a sulfate group, or serine (an amino acid) may be bound.

Basic substances for life, such as a nucleobase, sugar saccharide, an amino acid, and a fatty acid, and the like are molecules composed of some of or all the 6 elements, C, N, P, S, O, and H. Therefore, major substances contained in *Escherichia coli* cells are mainly composed of the 6 elements composing basic substances for life. Actually, about 14 inorganic elements are found in *Escherichia coli* cells in addition to these elements. Specifically, these 14 inorganic elements include 5 inorganic elements (e.g., Na, K, Mg, Ca, and Cl) and 9 trace metal elements (V, Mo, Se, Mn, Fe, Co, Ni, Cu, and Zn) (in the case of higher organisms, Cr is added to the 9 elements to result in 10 in total). Thus, the total of 14 elements plus the above 6 elements equals a total of 20 elements. The latter 14 inorganic elements and trace metal element are not included as member of elements constitutive of basic substances for life. However, in many cases, these 14 elements are found in association with major substances, thereby maintaining the conformation of a major substance that is a macromolecular substance such as DNA or protein, and playing an essential role in exertion of the functions of major substances such as enzyme activity.

1-2. Essential Elements

One of the currently available methods for determining the essential elements is as follows. This is a method that involves examining the supply of an element and the biological reactions, and then revealing whether or not the element is an essential element for the organism. Specifically, the method is a technique by which an element is determined to be essential for an organism when the supply of the element is gradually increased starting from none, and then the resulting biological reactions appear within a dose range, in as per the following order: no growth, weak growth or nutritional deficiency, accelerated growth, optimum growth, poor growth or indication of harmful symptoms, and impossibility in growth or death. For example, supposing that Zn, supplied in a low-concentration range, has an effect of delaying mouse growth. Zn, given in a slightly higher concentration, promotes the growth in an accelerated manner, but Zn given in a even higher concentration has an inhibitory effect. Under such a growth environment, Zn is regarded as an essential element for mice. The results are regarded as nutritional evidences indicating that the relevant element is essential. In the present invention, this method was applied to microorganisms. Specifically, Si is taken as an example for explanation. Si has not been regarded as an essential element for *Escherichia coli*. An Si compound containing Si element is added to an *Escherichia coli* growth medium. When *Escherichia coli* grows increasingly in a dose-dependent manner compared with that of no addition, and the intracellular content of the Si element in *Escherichia coli* increases, present inventor believe that the Si element is regarded as an essential element for *Escherichia coli* under the conditions employed.

2. Isolation of Microorganism Capable of Using Element that is not Generally Known to be Used by Microorganism The present inventors carried out a research for isolation of a microorganism capable of using silicate instead of an S source from a soil sample taken at natural environment. According to known examples of isolation of microorganisms, isolation was attempted using agar media of unique environment conditions created by varying the pH, temperature, salt concentration, and the like of media. As a result, colonies appeared in the agar medium; however, almost all colonies exhibited a tendency of attenuated growth after repetition (several times) of subculture in media of the same composition.

Next, the present inventors conducted another research in the same way as above, using *Escherichia coli* as a representative existing bacterium and a liquid medium. In this test, a liquid medium was prepared by adding sodium silicate to a synthetic medium containing all the 4 essential nutrients: appropriate amounts of a C source, an N source, and a P source and a limited amount of an S source. Washed *Escherichia coli* was used to seed into the liquid medium and then incubated at 37° C. On this occasion growth was clearly observed, and *E. coli* grew to a higher level than that in the control medium to which no silicate had been added. Furthermore, it was discovered that *E. coli* grew again even after subculture in medium of the same composition. Subsequently, it was further discovered that: *Escherichia coli* grew even when a general trace element other than silicate or a compound containing an element that had not been regarded as an essential element for microorganisms were used; and that under similar conditions, other bacteria, actinomycetes, yeast, filamentous fungi, and the like also grew. Thus, the present inventors completed the present invention.

3. Culture Method that Causes a Microorganism to Incorporate a Substitute Compound Containing a Substitute Element Substituting for an Essential Element 3-1. Medium 3-1-1. Nutrition-Deleted Medium In the present invention, a medium deleting one, two, or more elements from among C, N, P, and S is referred to as a nutrient-deleted medium.

An example thereof is a medium prepared by deleting only a nutrition source containing any one of the elements C, N, P, and S from a complete nutrition medium (denoted as "CM medium"). A specific example thereof is a medium prepared by deleting only an S source from a complete nutrition medium, so that it substantially lacks the S source and *Escherichia coli* cannot substantially grow even when seeded therein. Such a medium is denoted as an "S (−) medium." Similarly, in the case of deletion of other nutrition sources, an example thereof is a medium prepared by deleting only a C source, an N source, or a P source from a CM medium, so that it substantially lacks the C source, the N source, or the P source and *Escherichia coli* cannot substantially grow even when seeded therein. These media are denoted as a "C (−) medium," an "N (−) medium," and a "P (−)," respectively.

Here, the term "CM medium" refers to a medium appropriate for the growth of a microorganism such as *Escherichia coli* to be subjected to the present invention. For example, regarding *Escherichia coli*, an example of the CM medium has the composition containing essential nutrients for the growth of *Escherichia coli* (e.g., a C source, an N source, a P source, an S source, an inorganic material such as NaCl and a trace metal salt, and substances required as nutrients) in appropriate amounts, and enables *Escherichia coli* to grow approximately to a known amount at a known rate therein.

The present inventors mainly used two types of CM medium and modified media thereof. The composition thereof is as follows.

(a) GY medium: This was used for seed culture. Composition: glucose (10 mg/mL), yeast extract (5 mg/mL), peptone (10 mg/mL), NaCl (3 mg/mL), sodium glutamate (2 mg/mL), pH 6-7.

(b) CM medium: A synthetic inorganic salt medium. This was used for a growth test, for example.

(Concentration of ingredient (mg/mL)):

(C source) glucose (10 mg/mL), glycerol (5 mg/mL)

(N source) $NH_4Cl$ (1 mg/mL), urea (0.1 mg/mL)

(P source) $K_2HPO_4$ (0.6 mg/mL), $KH_2PO_4$ (1.4 mg/mL) Total: 2.0 mg/mL (S source) $Na_2SO_4$ (0.2 mg/mL)

(Inorganic salt (mg/mL)) NaCl (1.5 mg/mL), KCl (0.1 mg/mL)

(Metal salt) Mg (150 mcg/mL), Ca, Fe, and Zn (10 mcg/mL each), Mn, Cu, Co, Ni, Mo, and W (3 mcg/mL each)

(Amino acid) Arg. HCl (0.5 mg/mL), Asparagine (0.5 mg/mL), Glutamine (0.5 mg/mL), Lysine. HCl (0.5 mg/mL)

(Additive) The following substances were separately used as necessary.

A yeast extract (0.01-1.0 mg/mL), Tween20 (0.1 mg/mL), oleic acid Na (0.1 mg/mL), 2-ketoglutarate (0.1 mg/mL), biotin (0.01 or 0.001 mg/mL), a substance required as a nutrient (when a mutant strain requiring the nutrient was used), deionized water, pH 6.0-7.5 before the initiation of culture, test tubes containing 10 mL/100 mL of medium, Erlenmeyer flasks containing 20 mL/100 mL of medium, and Erlenmeyer flasks containing 120 mL/500 mL of medium, and the like were used.

Also, the expression in the present invention, "cannot substantially grow" means that cells can grow to a level only twice (or less) the amount of cells inoculated at the initiation of culture. Although seeded in a C (−), N (−), P (−), or S (−) medium prepared by deleting one of these essential nutrient sources, inoculated cells can grow in some cases. This can take place when a nutrient may also be inevitably brought together with the inoculated cells. However, such a growth is decreased as cells are subcultured, and it merely takes place temporarily.

In addition, for example, when an S(−) medium is prepared, an S-containing compound such as sulfate, S-containing amino acid, or sulfonate is not used upon selection of a C source, an N source, and the like. Similarly, since a complex natural nutrition source such as a commercially available yeast extract contains an S-containing peptide, the use thereof as a nutrition source for an S(−) medium requires attention. In the present invention, a synthetic inorganic salt medium was used as an S(−) medium. The same applies to a case when a C(−) medium, a N(−) medium, or a P(−) medium is prepared.

3-1-2. Nutrition-Limited Medium

In the present invention, a nutrient-deleted medium, which lacks any one, two or more of the above elements C, N, P and S and is supplemented with only a limited amount of a compound containing the deleted element, is referred to as a "nutrient-limited medium."

For example, a C source-deleted medium supplemented with a limited amount of a C source may also be described as "C ($\alpha$C)," an N source-deleted medium containing a limited amount of an N source may also be described as "N ($\alpha$N)," a P source-deleted medium containing a limited amount of a P source may also be described as "P ($\alpha$P)," and an S source-deleted medium containing a limited amount of S may also be described as "S ($\alpha$S)."

Also, the meaning of the term "limit(ed)" is explained as follows using a case in which an S source is limited, as an example. The concentration of a compound containing S (S-containing compound) is not necessarily strictly specified, as long as it is contained in a limited amount, and can account for 1% to 10% of the conventionally used amount of an S source in a CM medium. When the amount of an S-containing compound to be added is too low, no growth can take place. When the amount of the same is too high, cells seem to grow in a medium supplemented with a substitute compound (as explained later), however, the cells may actually grow using the S-containing compound. An amount within the range between them can be said to be a useful limited amount for the present invention. This can be varied depending on a microorganism to be used, a substitute compound to be contained in a medium supplemented with the substitute compound, and other conditions.

When a C source, an N source, or a P source is limited, similarly, the limited amount thereof is not necessarily strictly specified. The limited amount thereof may account for 1% to 10% of that of the C source, the N source, or the P source contained in a general CM medium.

3-1-3. Medium Supplemented with Substitute Compound (1) In the present invention, a medium prepared by limiting the amount of any one, two or more of the elements C, N, P and S above, and adding a compound (hereinafter, referred to as "substitute compound" or "X-containing compound") containing element X (hereinafter, referred to as "substitute element") alternative to the limited element is referred to as a medium supplemented with a substitute compound. When a substitute compound is added to a nutrient-limited medium prepared by limiting the amount of a C source, an N source, a P source, or an S source, the resultant can be described as a C($\alpha$C+X) medium, an N($\alpha$N+X) medium, a P($\alpha$P+X) medium, or an S($\alpha$S+X) medium.

Examples of such a substitute compound include inorganic or organic compounds usable for microorganisms, which contain, as a constitutive element(s), one, two, or more elements selected from the group of elements belonging to groups 3, 4, 5, 6, 13, 14, 15, and 16 of the 2nd, 3rd, 4th, 5th, and $6^{th}$ periods in the long form periodic table, from which C, N, P, S, and O are excluded.

Examples of an substitute element include Sc, Y, La, Nd, Eu, Er, Tb, Ti, V, Nb, Mo, W, B, Si, Ge, Sn, As, Sb, and Te. Specific preferable examples thereof include one, two, or more elements selected from the group consisting of La, Nd, Eu, Ti, V, Mo, W, B, Si, Ge, Sn, and Te. Further preferable examples thereof include Nd, Eu, V, Si, and Ge.

Examples of a substitute element of an inorganic compound or an organic compound can be exemplified as follows, wherein (AcO) denotes an acetyl group, (2PrO) denotes an isopropoxyl group, (EtO) denotes an ethoxy group, Me denotes a methyl group, and (MeO) denotes a methoxy group: (Sc)(2PrO)$_3$Sc, (Y)YCl$_3$, (Er)(2PrO)$_3$Er, (Yb)(AcO)$_3$Yb, (Ti)TiCl$_4$, (EtO)$_4$Ti, (Zr)ZrCl$_4$, (EtO)$_4$Zr, (V)Na$_2$VO$_4$, NH$_4$VO$_3$, (EtO)$_3$VO, (Nb)(EtO)$_5$Nb, (Mo)Na$_2$MoO$_4$, (W)Na$_2$WO$_4$, (B)Na$_3$BO$_3$, (MeO)$_3$B, (Al)AlCl$_3$, Me$_3$Al, (Si) Na$_2$SiO$_4$, Na$_2$SiO$_3$, water glass, Me(MeO)$_3$Si, (Ge)Et$_4$Ge, (EtO)$_4$Ge, (Sn)K$_2$SnO$_4$, (As)Na$_2$AsO$_4$, and (Te)K$_2$TeO$_4$.

Specifically, such a "substitute compound" is an oxide, or chloride of a substitute element, or the other types of inorganic compound, or an organic compound thereof. The term "substitute compound" refers to a compound that can be used by a microorganism seeded in a nutrient-limited medium supplemented with a substitute compound and these compounds. When an substitute element is X, an X-containing compound as a substitute compound may contains (1) an alkali metal salt or an ammonium salt of an oxide of X, (2) an inorganic acid salt or an organic acid salt of a base of X, and (3) a simple ester or ether prepared by binding a methyl group or an ethyl group to inorganic acid of X. Specifically, when X is Si, the X-containing compound contains silane. When X is B, it contains borane. For example, Me (MeO)$_3$Si (methyltrimethoxysilane) is contained.

Furthermore, an amino acid derivative, a sugar derivative, or a fatty acid derivative of an X-containing compound can be used, for example. Specifically, the compound may be a chemically synthesized compound containing element X or a compound derived from a natural product. An X-containing compound that can be used herein may be a monomer or a polymeric X-containing compound, such as a dimer, a trimer, or a tetramer.

As these compounds to be used can be, either water-soluble substances or water-insoluble substances.

The total amount of a substitute compound may be added to a medium at once, or it may be divided into portions and then the portions may be added separately and intermittently.

When multiple substitute compounds are added, the amount of growth may further be increased than the case of addition of a single substitute compound.

A medium may be in a liquid, a solid, or a semifluid form in any of the above cases.

(2) Amount of substitute compound added

The amount of a substitute compound to be added can be examined as follows.

In a synthetic medium containing a constituent compound having a known concentration (as in a published literature), the concentration of an S source compound ranges from about 0.1 g/L to 1 g/L. When ammonium sulfate is used as an N source, the concentration may be higher than such an example.

A substitute compound to be added to a medium is regarded as a S source substitute. Hence, the concentration of such a substitute compound to be added is determined according to the concentration of an S source compound as described in published literature. Specifically, the concentration of such a substitute compound ranges from 0.1 g/L to 1 g/L and preferably ranges from 0.1 mM to 50 mM. However, the concentration thereof may differ depending on microorganisms and/or culture conditions.

The limited amount of an S source preferably accounts for about 1%-10% of that of an X compound. However, the limited amount thereof is not limited thereto and may differ depending on strains or culture conditions.

It is generally useful to add a trace amount of a complex natural nutrient such as an yeast extract, to a medium as an agent for accelerating microbial growth. In the present invention, it is often required and useful to add a trace amount of such a complex natural nutrient to a medium supplemented with a substitute compound. However, such a complex natural substance is a growth accelerator and can also be an essential nutrient source (e.g., C, N, P, or S source), at the same time. In the present invention, even when a complex natural nutrient is added to a nutrient-deleted medium not supplemented with a substitute compound or a nutrient-limited medium, such an addition is not regarded as the addition of a C, N, P, or S source, as long as the amount thereof added herein is within a range such that it does not cause a change in the amount of microbial growth. When a yeast extract is added at 0.5 mg/mL or less to a C(−) medium, this addition did not affect the amount of *Escherichia coli* growth. Thus, the amount of the yeast extract in this case is not considered as the limited amount of a carbon source ($\alpha$C). Similarly, under conditions employed by the present inventors, 0.05 mg/mL or less of a yeast extract is not considered as a limited amount of an N or a P source, and 0.01 mg/mL or less of the yeast extract is not regarded as a limited amount of an S source.

The pH for a CM medium, an S(−) medium, an S(X) medium, or an S(X+$\alpha$S) medium is not particularly limited. In the case of *Escherichia coli*, the pH of a medium preferably ranges from 5 to 8.

When a microbial strain is a strain requiring a nutrient, and specifically, when it requires the presence of an S-containing compound such as methionine or biotin for its growth, the minimum amount of such a compound must be added to the medium to satisfy the nutritional requirement.

Other Additives

When a small amount of fatty acid, 2-ketoglutarate, or a yeast extract is added to a growth test medium, microbial growth may be accelerated in an S(X) medium in some cases. Examples of fatty acid to be added herein include C10-C18 saturated or unsaturated fatty acids. In this case, the mechanism by which microbial growth is accelerated currently remains unknown.

The ratio of a C source, an N source, a P source, and an S source to be added can be determined in reference to media described in microbiology books.

Cases in which *Escherichia coli* is cultured in a S-limited medium supplemented with an X-containing compound are explained above as examples.

(3) Notation for medium

When cells are cultured in a medium supplemented with an X-containing compound under conditions where the amount of a source (P source, N source or C source) other than S source is limited, the following media can be used, for example:

CM medium, P(−) medium, P($\alpha$P) medium, P(X+$\alpha$P) medium

CM medium, N(−) medium, N($\alpha$N) medium, N(X+$\alpha$N) medium

CM medium, C(−) medium, C($\alpha$C) medium, and C(X+$\alpha$C) medium.

A further required nutrient and an amino acid (it may also be abbreviated as "a" or "aa"), a yeast extract (it may be denoted as "Y"), a fatty acid (it may be described as "f"), and/or 2-ketoglutarate (it may be abbreviated as "k") for accelerating the growth may be added to an S(X+$\alpha$S) medium, a P(X+$\alpha$P) medium, an N(X+$\alpha$N) medium, or a C(X+$\alpha$C) medium. Notation for media in these cases is as described below. For example, when an yeast extract (Y) and 2-ketoglutarate (k) are added to the N(X+$\alpha$N) medium, the medium is denoted as N(X+$\alpha$N)Yk medium. Similarly, when fatty acid (f) and amino acid (a) are added to the S(X+$\alpha$S) medium, the medium can be described as (X+$\alpha$S)f medium. When additives other than X and $\alpha$P are added to the P(X+$\alpha$P) medium, the medium is denoted in the same manner, such as a P(X+$\alpha$P)Ya medium or a C(X+$\alpha$C)Ya medium.

When bacteria other than *Escherichia coli*, yeast, and filamentous fungi are cultured, it is desirable to select a medium and culture conditions appropriate for each of them. The purpose can be achieved using only one medium according to the purpose of a test. The pH of a medium and the temperature for culture are not particularly limited, as long as microorganisms can grow. In the case of general microorganisms, the temperature for culture ranging from 10° C. to 45° C. can be employed. When a thermophilic microorganism is used, it should be cultured at a temperature even higher than the above range. Also, microorganisms grow at the pH ranging from 1 to 12.

The concentration of an S-containing compound to be added to the S(X+$\alpha$S) medium is not necessarily strictly specified, as long as the amount thereof is within the limited amount thereof. When the amount thereof to be added is too low, the growth is decreased or does not take place. When the amount thereof is too high, the microorganism may actually grow using the S-containing compound added, even if it seems to grow in the S(X+$\alpha$S) medium. An amount within the range between them can be said to be a useful limited amount for the present invention. This can be varied depending on a microorganism to be used, an X compound, and other conditions. However, as described above, determination can be made using a difference in the amount of growth between two media as an indicator. Specifically, determination can be made using as an indicator whether or not there is a clear difference between the amount of microbial growth in the S(X+$\alpha$S) medium and the amount of microbial growth in an S($\alpha$S) medium (that is a control medium to which no X has been added). This is an indicator for determining X compound-dependent growth and can be an evidence to determine that cells are the microbial cells of the present invention.

The S(X) medium and the S(X+$\alpha$S) medium are disclosed for the first time in the present invention. There are no conventional studies to search for novel microorganisms using these kinds of medium. Examples thereof include an S(X)

medium supplemented with a 3$^{rd}$ component. For example, an S(X)Y medium supplemented with a small amount of a yeast extract is encompassed in the present invention. Furthermore, an S(−) medium and a solution of an X-containing compound are separately prepared and then the X-containing compound is added during use or culture. This is also encompassed in the present invention.

3-2. Method for Culturing Microorganism

In the present invention, strains preserved in culture collection institution or laboratories, wild-type strains isolated from nature, clinical isolates, and mutant strains obtained by genetic recombination or a method using an artificial mutation agent can be used.

The present inventor have discovered that a microorganism can be caused to incorporate an substitute element as a constitutive element of the microbial cell by a culture method that comprises culturing the microorganism in a medium supplemented with a substitute compound, which is prepared by adding a limited amount of any one element of nutrition sources (C, N, P, and S) in the medium and adding the compound (substitute compound) containing an element alternative to the element (substitute element).

Examples of the method include the following methods.

3-2-1. Method for culturing a microorganism in a medium prepared by limiting a nutrition source of the element C, N, P, or S (that is generally an essential element in the medium) and then adding a compound containing an substitute element that can be a substitute for the element (the amount of which is limited).

3-2-2. Method for adaptation culture. Specifically, by repetition of subculture in a medium supplemented with a substitute compound, the substitute element can further be efficiently incorporated into a microorganism. Regarding the appropriate adaptation culture period, in general, adaptation culture may be carried out for a period of single subculture, but the example thereof is not limited thereto. Adaptation culture can be carried out at the same time as the 1$^{st}$ seed culture and the 2$^{nd}$ seed culture.

3-2-3. Method that comprises subjecting cells obtained by seed culture to starvation culture, and then culturing cells in a medium supplemented with a substitute compound.

Starter cells are subjected in advance to starvation culture for a predetermined period in a medium in which the nutrition to be limited is not contained. After exhaustion of a nutrient of C, N, P, or S source remaining within cells, the culture method described in 3-1-3 above can be employed for culturing cells in a medium supplemented with a substitute compound. An appropriate starvation culture period is generally one subculture time, and appropriately ranges from several hours to 24 hours. Starvation culture may be repeated for two or more times of subculture, when necessary. The completion of starvation culture can be determined by using as an indicator the cell concentration at the initiation of starvation culture, such as turbidity (optical density (OD)) as measured by nephelometry, becomes stationary upon continuation of cultivation. However, it is varied depending on the type of the microorganism and culture conditions before starvation culture and particularly medium composition. Upon starvation culture, a substitute compound may or may not be added to a medium.

By doing in this manner, it is possible to cause a microorganism use efficiently a substitute compound containing a substitute element, and to grow in dose-dependent manner, so as to be able to cause the microorganism to incorporate the substitute element as a constitutive element of the cells.

3-2-4. Use of mutant strain

As described above, a method for growing a microbial strain under conditions where the amount of a C source, an N source, a P source, or an S source is limited and a substitute compound (X compound) is added is effective to cause the microbial strain to be used herein to efficiently incorporate the X compound. Limitation of the amount of an essential nutrient source for a microorganism can also be performed by a method other than the changing of the medium composition. For example, the same effect can be expected using a mutant strain having poor or lacking capacity for allowing a C source, an N source, a P source, or an S source to pass through cell membrane, or a mutant strain having poor or lacking capacity for metabolizing the C source, the N source, the P source, or the S source. An example thereof is a mutant strain that requires a sulfur-containing amino acid and is derived from the *Escherichia coli* K-12 strain, such as the NBRC3993 strain that is in the possession of culture collection institution, as described in Examples.

A mutant strain having enhanced microbial capacity for incorporating an X-containing compound, such as a mutant strain prepared by extracting a receptor for an X-containing compound from cells of a different species and then incorporating it by a recombination technique, a mutant strain exhibiting enhanced receptor protein expression, and the like, can also be used herein. Moreover, a mutant strain having increased usability for X can also be used herein.

Also, such a mutant strain can also be used in combination with the above culture method.

4. Presumed Mechanism of Starvation Culture to Accelerate Incorporation of Substitute Compound A mechanism for accelerating the use of a substitute compound in strains obtained by starvation culture or metabolism-deficient mutant strains, which is presumed from literature, are as follows.

In the incorporation of a substitute compound a mechanism involving a receptor protein is thought to function. It is known that when cells are starved because of the shortage of any one of nutrition sources (C source, N source, P source, and S source), the expression of a protein involved in the incorporation system is enhanced. When *Escherichia coli* or the like is deficient in an N source, the expression of the gene of transporter protein (referred to as "transporter") for an $NH_4$ and a nitric acid groups, and of glutamine synthase for assimilation the incorporated N source compound is enhanced. When a substitute compound is incorporated via the incorporation system like the above, it can be understood that accelerated incorporation by N starvation culture is achieved by the above mechanism.

5. Microbial Cells

Cells obtained by the method of the present invention contain an substitute element as a constitutive element.

An substitute element can be introduced into *Escherichia coli* using a medium prepared by deletion or limitation of the amount of a C source, an N source, a P source, or an S source. This can be similarly carried out for other bacteria, fungi, and basidiomycetes. Moreover, through application of gene recombination techniques, the incorporating capacity of a receptor can be enhanced, lowered, changed, or deleted.

It is believed that a substitute compound added to a medium is incorporated into cells, and then used as an essential element to constitute a cell structure material. It is considered that a substitute compound is incorporated by behavior similar to that for an essential element.

When a substitute compound is used as a C source substitute, the Si element content in cells is 50 ppm or higher. When a substitute compound is used as a N source, a P source, or an S source substitute, the Si element content in cells is 5 ppm or higher. Meanwhile, also in published literature, an example of the elemental composition of cells are: Si 40 ppm, Sn, Mo, B, or V is 1 ppm or less (E. Ochiai "Bioinorganic Chemistry, An Introduction" Allyn and Bacon, Inc. 1977). Specifically, these contents are higher in the cells of the present invention.

The amount of microbial growth increases in a dose-dependent manner compared with a control to which no substitute compound has been added. The thus incorporated Si is distributed in sites containing cell wall fractions and protein fractions.

When cells obtained in the present invention are subcultured for five times or more, they maintain basically the same properties. On the other hand, it has not been revealed if microbial cells to which harmful substances (e.g., Cd, Pb, and Cr) have been adsorbed can maintain the same properties even after subculture.

The microbial cells of the present invention can be groupfied into a strain differing from the original strain, when classified based on chemical classification. The microbial cells of the present invention grown using an Si-containing compound differed from the original strain in the following points.

Size changes were observed under a microscope.

The microbial cells contained a non-essential element, the presence of which within microbial cells was observed for the first time.

Immune response of the in cell wall fractions changed.

It was suggested that the microbial cells contain amino acids differing from the 20 types of amino acid. This may be due to the incorporated elements binding to known amino acids.

The actinomycetes of the present invention produced an antibiotics. The structure thereof is expected to differ from the antibiotics to be produced by the original strain.

6. Growth in Medium Supplemented with Substitute Compound and Verification of Incorporation of Substitute Element by Microorganism 6-1. Growth Analysis A method for analyzing the microorganisms of the present invention is as explained below.

The amount of microbial growth to be used in the present invention can be measured by a conventional microbiological method. Specific examples thereof include turbidometry, an MTT method, a method for determining dry cell weights, and a colony counting method. The present inventors often used turbidometry for quantifying *Escherichia coli* growth.

Bacterial cells are generally suspended uniformly, and thus turbidometry can be applied. However, filamentous fungi or actinomycetes often grow while forming pills with a diameter of 1-5 mm during liquid culture without being uniformly suspended. Turbidometry cannot be used in this case, but the MTT method or the like can be used instead of turbidometry.

6-2. Verification of Incorporation of an Substitute Element as an Essential Element into Cells According to a theory of bioinorganic chemistry, when the amount of microbial growth in the S(X+αS) medium is higher than that in a control S(αS) medium to which no X-containing compound has been added, this is considered as growth depending on the X-containing compound. If the growth is dependent on the dose of an X-containing compound, X compound-dependent growth is confirmed. In this case, it is considered that the X element of the X-containing compound is chemically converted along the metabolic flow to result in a necessary substance. Specifically, in this case, the X element is likely to function as an essential element.

Accordingly, in the present invention, when a microorganism grows in a dose (substitute element (X-containing compound))-dependent manner, it is concluded that the substitute element is essential for the microorganism.

In the present invention, to confirm X-containing compound-dependent growth, for example, when S was limited, a difference between the amount of microbial growth in the S(X+αS) medium and the same in the control S(αS) medium (to which nothing of X-containing compound had been added) was measured. When a C source, an N source, or a P source is limited, such a difference can be similarly measured using the C source, the N source, or the P source instead of the above S source.

6-2-1. Elementary Analysis

It is an important object of the present invention to verify elements contained in microbial cells. The following methods can be used therefor. When a positive result can be obtained by the analysis method exemplified below, this indicates not only the fact that the element is contained, but also a possibility such that *Escherichia coli* grew depending on an X compound containing element X, such as an Si-containing compound, or *E. coli* grew using Si as an essential element.

All elements contained in cells can be analyzed by Inductively Combined Plasma Ion Trapping Mass Spectrometry (that is, ICP-MS method) or ion pair chromatography, for example. For analysis of specific elements, photoelectric colorimetry or the like, by which elements can be selectively detected and quantified, can be used.

6-2-2. Elementary Analysis of Cells (Whole Cell Analysis)

Cells obtained by growing *Escherichia coli* in the presence of an X compound containing element X such as a Si-containing compound are washed and inactivated. Cells of infectious microbial strains such as *Escherichia coli* are inactivated before measurement. Heat treatment, sterilization using formalin or beta-Propiolactone, or the like can be used for inactivation.

Subsequently, elements in all cells are analyzed by an ICP-MS method, ion pair chromatography, or another instrumental analysis method. As control cells, *Escherichia coli* cells grown in the absence of an X element compound are similarly treated and then the results are compared.

(Analysis of Elements in Microbial Fractions)

Elements can be analyzed using *Escherichia coli* cell fractions instead of all cells. *Escherichia coli* cells are subjected to an ultrasonic disintegrator or a French press for cell disruption. Disrupted cells are centrifuged, a precipitate portion (containing cell walls) or a soluble supernatant portion (containing proteins) is subjected to elementary analysis. Thus, the presence or the absence of the element X in this fraction can be verified.

(Analysis of Binding and Non-Binding Elements)

Microbial cells obtained by culture in test media are dialyzed against water under low-temperature conditions. Free compounds within cells are diffused for removal, and then elements within cells are analyzed. The thus detected elements are considered as binding elements existing within cells.

Cells treated with acetone can be used for the same purpose. Lipids in cell surface layers are eluted by treatment of cells with acetone, so that free compounds existing within cells can be easily diffused out of cell walls. When cells treated with acetone are left to stand in water-containing acetone overnight, only the bound form from among X compounds incorporated into cells remain within cells. The binding substances are then detected.

6-2-3. Amino Acid Analysis Method

Whether or not element X is incorporated into a protein fraction can be verified by hydrolyzing the protein under acidic conditions and then conducting amino acid analysis. The number of types of amino acid constituting a protein is known to be 20. Hence, when peaks indicating those other than the 20 types are observed, substances of the new peak included therein may be subjected to further analysis in detail.

EXAMPLES

The following test examples and media to be used in Examples and preparation procedures are as shown in Tables below.

A method for preparing media of the present invention is as explained in Section 3-1. Nutrient-deleted media, nutrient-limited media, and media supplemented with substitute compounds are used herein. Preparation of nutrient (S source)-deleted media, nutrient (S source)-limited media, and media supplemented with substitute compounds for an S source are specifically explained herein as examples.

First, an S(−) medium that is A. a minimal essential medium is prepared. The S(−) medium denotes a medium not supplemented with a compound as an S source. The medium composition is as described in Table of medium (Table 1-1) showing medium composition. Microorganisms are substantially unable to grow in this medium. Oleic acid (abbreviated as "f"), amino acid (including 2 types of mixture, "a" and "aa", are available), and glutamic acid Na to be added as a buffering agent to an S-series of medium are added to the S(−) medium. Thus, S (−)fa that is a B. nutrient-deleted medium is prepared. This medium is used for S source starvation culture. Next, a limited amount of an S source and yeast extract (abbreviated as "Y") are added to the S (−) fa medium, so that S (αS)Yfa medium, that is a nutrient-limited medium, is prepared. Finally, an X-containing compound comprised of element X to be incorporated is added, so that D. medium S (αS+X)Yfa supplemented with a substitute compound is prepared. P source- or C source-series of nutrient-deleted media, nutrient-limited media, and media supplemented with substitute compounds are prepared by similar procedures.

TABLE 1-1

Medium composition Example 1. Preparation of minimal essential medium (MEM)

| A MEM | Ingredient | S(−) medium | P(−) medium | N(−) medium | C(−) medium |
|---|---|---|---|---|---|
| C source | Glucose (g/L) | 10 | 10 | 10 | (−) |
|  | Glycerin I | 5 | 5 | 5 | (−) |
| N source | NH4Cl | 1 | 1 | (−) | 1 |
|  | Urea | 0.1 | 0.1 | (−) | 0.1 |
| P source | Potassium phosphate | 2 | (−) | 2 | 2 |
| S source | Na2SO4 | (−) | 0.2 | 0.2 | 0.2 |
| Salts | NaCl | 1.5 | 1.5 | 1.5 | 1.5 |
|  | KCl | 0.1 | 0.1 | 0.1 | 0.1 |
| Metal ions (mg/L) | Mg2+ (150), Ca2+ (10), Fe2+ (10), Zn2+ (10), Mn2+ (10), Cu2+ (3), Co2+ (3), Ni2+ (3), Mo2+ (3), W2+ (3) | | | | |
| Redistilled water | pH | pH 6.5 | pH 6.5 | pH 6.5 | pH 6.5 |

TABLE 1-2

Medium composition Example 2. Preparation of medium supplemented with substitute compound

| A. Minimal essential medium | | S(−) medium | P(−) medium | N(−) medium | C(−) medium |
|---|---|---|---|---|---|
| Additive | (g/L) | (f) Oleic acid Na 0.1 | | (k) 2ketoglutaric acid Na 0.1 | |
| Amino acid (a) + (aa) | (g/L) | (a) 4 + (aa) 0.8 | (a) 2 + (aa) 0.8 | (−) | (−) |
| Buffering agent | (g/L) | Glutamic acid Na 8 | Glutamic acid Na 8 | Potassium phosphate, 8 | Potassium phosphate, 8 |
| B. Nutrient-deficient medium | | S(−)fa | P(−)a | N(−)k | C2(−) |
| α + yeast extract (Y) | added (g/L) | αS + (Y) 0.1 | αP + (Y) 0.1 | αN + (Y) 0.05 | αC + (Y) 0.5 |
| C. Nutrient-limited medium | | S(αS)Yfa | P (αP)Ya | N (αN)Yk | C(αC)Y |
| Substitute compound | added | X | X | X | X |
| D. medium supplemented with substitute compound | | S(αS + X)Yfa | P (αP + X)Ya | N (αN + X)Yk | C(αC + X)Y |

Amino acid (a): Gln (L-glutamine) + Asn (L-asparagine) + Lys•HCl (L-lysine) + Arg•HCL (L-arginine) (1 g/L each)
Amino acid (aa): 20 types of L-amino acid. However, S(−)Yfa medium was not supplemented with sulfur-containing amino acids (Met (L-methionine) and CysH (L-cysteine)).

Furthermore, abbreviations and compounds corresponding thereto used in the following test examples and Examples are as listed in Table 2 below.

TABLE 2

Names of compounds and abbreviations (1)

| Group * period | Symbol of element- Name of element | Abbreviation of compound | Japanese name of compound | English name of compound |
|---|---|---|---|---|
| 3 * 6 | La, Lanthanum | hLa | 水酸化ランタン (無水物) | Lanthanum (III) hydroxide, anhydrous |
|  | La, Lanthanum | pLa | ランタンイソプロポキシド | Lanthanum (III) isopropoxide |
| 3 * 6 | Ce, Cerium | hCe | 水酸化セリウム | Cerium (III) hydroxide |
| 3 * 6 | Nd, Neodymium | hNd | 水酸化ネオジム | Neodymium (III) hydroxide |
|  | Nd, Neodymium | pNd | ネオジムイソプロポキシド | Neodymium (III) isopropoxide |
| 3 * 6 | Eu, Europium | acEu | ユーロピウムアセチルアセトナート | Europium (III) acetylacetonate |
| 3 * 6 | Tb, Terbium | acTb | テルビウムアセチルアセトナート | Terbium (III) acetylacetonate |
| 3 * 6 | Er, Erbium | pEr | エルビウムイソプロポキシド | Erbium isopropoxide |
| 4 * 4 | Titanium | eTi | チタンエトキシド | Titanium (IV) ethoxide |
| 5 * 4 | V, Vanadium | V | オルソバナジン酸ナトリウム | Sodium orthovanadate |
| 5 * 5 | Nb, Niobium | eNb | エトキシネオビウム | Pentaethoxyneobium |
| 6 * 5 | Mo, Molybdenum | Mo | モリブデン酸ナトリウム | Sodium molybdate |
|  |  | 7Mo | モリブデン酸アンモニウム | Ammonium (hepta)molybdate tetrahydrare |
| 6 * 6 | W, Tungsten | W | タングステン酸ナトリウム | Sodium tungstate |
|  |  | 12W | タングステン酸アンモニウム五水和物 | Ammonium tungstate pentahydrate |

Abbreviations for compounds are as described in Tables or graphs in Examples. Table 2 clearly shows the meanings of the abbreviations.

TABLE 3

Names of compounds and abbreviations (2)

| Group * period | Symbol of element- Name of element | Abbreviation of compound | Japanese name of compound | English name of compound |
|---|---|---|---|---|
| 13 * 2 | B, Boron | B | ホウ酸 | Boric acid |
|  |  | BB | 硼砂 (ホウ酸ナトリウム) | Borax or sodium borate |
|  |  | mB | 三メトキシホウ素 | Trimethoxyborane |
| 14 * 2 | C, Carbon |  |  |  |
| 14 * 3 | Si, Silicon | CaSi | ケイ酸カルシウム(水和物) | Calcium silicate |
|  |  | dSi | 二ケイ酸ナトリウム (水和物) | Sodium disilicate |
|  |  | mSi | メタケイ酸ナトリウム | sodium metasilicate |
|  |  | wSi | ケイ酸ナトリウム溶液 | Sodium silicate solution |
|  | Si. Silicon | pSi | 四イソプロピルケイ酸 | Tetraisopropyl silicate |
|  |  | ESPA | 3-(トリエトキシシリル)プロピルアミン | 3-aminopropyltriethoxysilane |
|  |  | emSi | ジエトキシジメチルシラン | Diethoxydimethylsilane |
|  |  | mmSi | メチルトリメトキシシラン | Methyltrimethoxysilane |
|  |  | eSi | 四エチルケイ酸 | Tetraethyl silicate |
| 14 * 4 | Ge, Germanium | eGe | テトラエトキシゲルマニウム | Tetraethoxygermane |
| 14 * 5 | Sn, Tin | kSn | スズ酸カリウム | Potassium stannate |
| 15 * 2 | N, Nitrogen |  |  |  |
| 15 * 3 | P, Phosphorus |  |  |  |
| 15 * 4 | As, Arsenic | As | ヒ酸ナトリウム | Sodium arsenate |
| 15 * 5 | Sb, Antimony | Sb | ヘキサヒドロキシアンチモン(V)酸カリウム | Potassium hexahydroxo-antimonate |
| 16 * 2 | O, Oxygen |  |  |  |
| 16 * 3 | S, Sulfur | S | 無水硫酸ナトリウム | Sodium sulfate, anhydrous |
|  |  | SS | 二硫酸カリウム(水和物) | Potassium disulfate, hydrate |
| 16 * 4 | Se, Selenium | Se | セレン酸ナトリウム | Sodium selenate |
| 16 * 5 | Te, Tellurium | Te | テルル酸ナトリウム | Sodium tellurate |

Table 3 is a continuation from Table 2.

Test Example 1

The growth characteristics of an *Escherichia coli* mutant strain, *E. coli* K-12 (NBRC3993), were examined.

GY medium (a nutrient-rich medium) and S(−)fa medium (an S source-deleted medium) were used. The medium composition is as described in the next section.

In a test tube (denoted as "TT"; size 2.6×18 cmφ) containing 10 mL of a medium prepared by adding an S-containing compound to an S(−)fa medium, NBRC3993 was cultured shaking at 37° C. for 1 day. Subsequently, the amount of growth was measured by turbidometry. The results are shown in Table 4.

TABLE 4

| Additive (mg/mL) for S(−) fa medium | Amount of *E. coli* K12NBRC3993 growth OD660 × 10 d (cultured for 1 day) |
|---|---|
| No addition (−) | 0.050 |
| Sodium sulfate (0.2) | 0.144 |
| L-cysteine (0.05) | 0.240 |
| L-cysteine (0.05) + L-methionine (0.05) | 0.440 |
| Yeast extract (2.0) | 0.252 |

It is understood from the results in Table 4 that NBRC3993 is a strain requiring cysteine and/or methionine.

It was revealed that, in an attempt to incorporate X compound under limitation of S source, the X compound was incorporated more efficiently in strain NBRC3993 than in the parent strain *E. coli* K-12. This is described in Examples.

Example 1

The growth of bacteria and fungi (3 strains) was examined when cultured in C(αC+X) media each prepared by adding a limited amount of a C source (denoted as "αC") and an organic silicon compound as a C source substitute compound (denoted as "X") to a C source-deleted medium (C(−) medium).

(Method)

The following 3 strains were used. C source starved culture cells of each strain were used as starter cells.

Strain 1: *E. coli* K12 NBRC3301 (left 3 in FIG. 1),
Strain 2: *B. subtilis* (former natto) NBRC13169 (middle 3 of FIG. 1),
Strain 3: *Saccharomyces cerevisiae* NBRC0268 (right 2 in FIG. 1).

Medium: A C source-deleted medium (C(−) medium) was used for C source starvation culture. A C (αC+X) Y medium prepared by adding a limited amount of a C source (αC), an X-containing compound, and a yeast extract (Y) to a C(−) medium was used for a growth test. As such a limited amount of the C source (αC), a mixture of a yeast extract (Y) (0.5 mg/mL) together with glutamic acid Na (denoted as "glu" in Table (1 mg/mL)), lactate Na (denoted as "lac" in Table (0.5 mg/mL)), or glucose (denoted as "glc" in Table (0.5 mg/mL)) was used. As a buffering agent, a phosphate buffer (KH$_2$PO$_4$—K$_2$HPO$_4$, pH 6.4) (8 mg/mL) was added.

C source substitute compound (X): eSi (tetraethyl silicate) and emSi (diethoxydimethylsilane) were used. The amounts thereof added are as shown in FIG. 1.

Culture Conditions: 10 mL/TT, 33° C., 160 rpm

Seed culture, starvation culture following thereto, growth test culture and others the like were carried out as described below.

Starter cells were cultured in GY medium (glucose (10), peptone (10), yeast extract (5), NaCl$_3$, monosodium glutamate (2), pH 7) at 33° C. overnight (for one day and one night), and then cells were collected by centrifugation. Cells were washed twice by centrifugation in a phosphate buffered washing solution. While the cell concentration was adjusted to OD at 660 nm of about 5, washed cells were suspended again in a C(−) medium. The resultant suspension was shaken at 30° C. (that is, in C starvation culture conditions). The suspension with OD5 was used as starter cells, and inoculated at 5-7% (v/v) to the medium for test, and then the resultant was subjected to shaking culture at 33° C. and 160 rpm. A small amount of the resultant was collected on day 2 (d2) and then diluted 10-fold with water. The OD of the thus obtained solution was measured at 660 nm, so as to estimate the amount of growth.

(Result)

The results are shown in FIG. 1. The amount of growth (OD value) of strain *E. coli* K12 increased compared with that of the control (no C source substitute compound was added) when a silane had been added as a C source substitute compound in the presence of a limited amount of the C source. It was predicted that the silicon compound used herein would lead to the generation of silicate and ethanol in a culture solution. Hence, ethanol was added in an amount equimolar to that of an ethyl group in emSi for comparison. As a result, the OD was found to be lower than that of emSi. Therefore, it was considered that strain *E. coli* K12 grew with the use of Si in emSi. A similar tendency was also observed for other 2 strains.

Example 2

A C source-limited medium (C(αC) medium) was prepared by adding a limited amount of lactate Na as C source (denoted as "αC") to a C source-deleted C (−) medium. *Escherichia coli* growth was then examined using a C(αC+X) medium prepared by adding a methyl group-containing organic silicon compound mmSi (methyltrimethoxysilane (see Tables 2 and 3 for abbreviations for the compound)) to the C(αC) medium as a C source substitute compound; that is, an X-containing compound. Moreover, the effects resulting from adaptation culture were examined (specifically, after completion of the 1st (T1) culture, 2nd subculture (T2) was started in a medium of the same composition).

(Method)

Figure 2:
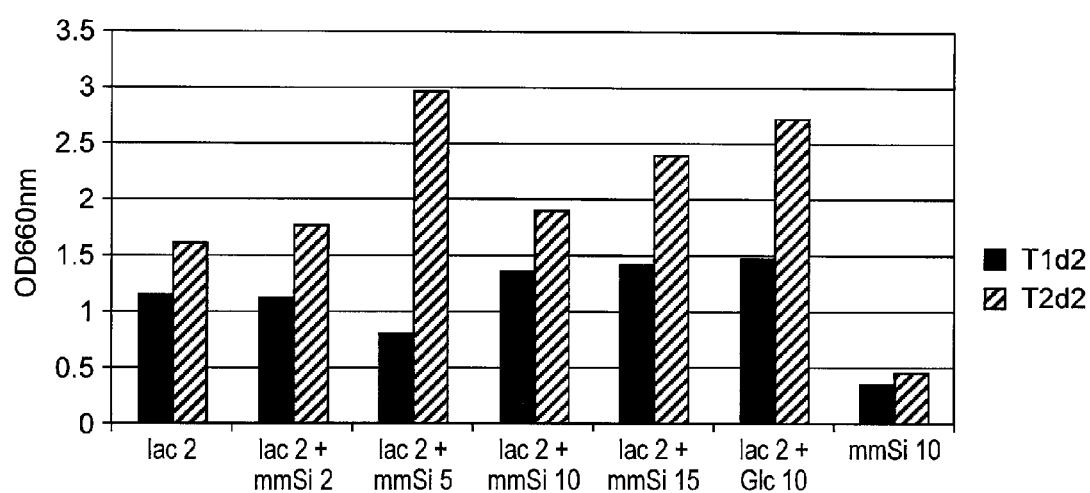
FIG. 2 shows the results of examining the growth of *Escherichia coli* using a C source-limited medium supplemented with a small amount of organic acid and a methyl group-containing organic silicon compound mmSi as a C source substitute compound.

C source-starved culture cells of *E. coli* K12 were used.
Strain 1: *E. coli* K12 NBRC3301,
Medium: A C (αC+X)Y medium was used.
Limited amount of C source (αC): lactate Na (denoted as "lac" in Figures (2 mg/mL))+yeast extract (Y) 0.5 mg/mL.
C source substitute compound: X: mmSi (methyltrimethoxysilane). The amounts of the compounds added are shown in FIG. 2.
Culture conditions: 100 mL/Erlenmeyer flask; 33° C.; and 130 rpm. At the time of completion of the 1st culture of, a portion of the culture fluid was pipetted off. Cells were washed by centrifugation and then seeded in a medium of the same composition. The OD value at the initiation of the subculture was adjusted to be close to the initial OD value of the 1st culture generation.

(Results)

The results are shown in FIG. 2. In a manner similar to that in Example 1, *E. coli* K12 starter cells were grown in a GY medium, cells were washed, and then subjected to C source starvation culture. The resulting cells were seeded as starter cells in a medium. On day 2, the 1st culture (denoted as "T1d2" in FIG. 2) cells were washed and then the cells were seeded as starter cells in a medium of the same composition for 2nd subculture for adaptation. On day 2 of the 2nd subculture (T2d2), the growth was measured.

The OD value of *E. coli* K12 increased when mmSi was added as a C source substitute compound, compared with the control (containing only a limited amount of the C source) to which no Si compound was added. Increases in OD value were in a dose-dependent manner. A tendency was observed such that the amount of growth in the 2nd subculture was higher than that of the 1st subculture. It is predicted that mmSi (silicon compound used herein) could generate silicate and methanol in the culture fluid. It is not known that *E. coli* is capable of using methanol. Actually, *E. coli* did not grow on mmSi alone (rightmost in FIG. 2) under the conditions employed herein. Therefore, it is considered that increases in OD value were the results of its use of the Si portion in mmSi. The result also indicates that even if there is a slight difference in OD value between of the 1st subculture and the control (to which no Si compound had been added), the difference in OD value between the control and of the 2nd subculture (or later) can become larger than the aforementioned difference.

Example 3

The results of measuring the amounts of growth in media containing silicon compounds used therein by colony counting method are described.

(Method)

The following 3 strains were used. C source starved culture cells of each strain were used as starter cells.

Strain 1: *E. coli* K12 NBRC3301,

Strain 2: *B. subtilis* (former natto) NBRC13169,

Strain 3: *Corynebacterium glutamicum* NBRC12168.

Medium: A C source-deleted medium (C(−) medium), a C source-limited medium, and a medium supplemented with a substitute compound (C (αC+X)Y medium) were used. A limited amount of lactate Na (described as "lac" in Figures" (2 mg/mL)) or glucose (described as "glc" in Figures. (2 mg/mL)) was added as a C source (αC) to a medium. In addition, a yeast extract (Y) was added at 0.5 mg/mL to each medium. In addition, strain 3 (*Corynebacterium glutamicum* NBRC12168) is a strain requiring biotin. Hence, biotin (5-10 mg/L) was added to a medium. C source substitute compound: R—Si: CaSi (calcium silicate), emSi (diethoxydimethylsilane), or borax (BB).

A phosphate buffer ($KH_2PO_4$—$K_2HPO_4$, pH 6.4) (8 mg/mL) was added as a buffering agent.

Culture Conditions: 10 mL/TT, 33° C., 160 rpm

Test strains were subjected to seed culture and starvation culture in a manner similar to Example 1 and then used. The amount of growth was determined by measuring optical density (OD) at 660 nm or by counting the number of colonies. CaSi is insoluble in water and causes white turbidity in a medium when added at 10 mg/mL to a medium. Accordingly, the result obtained by colony counting is more reliable. The colony method is carried out by seeding a diluent obtained by 10-fold serial dilution of a culture solution to a GY agar medium, keeping the temperature at 35° C. for 2 days, and then counting the number of colonies. On the other hand, BB used in parallel for the test was soluble in water. Hence, the growth in a culture broth solution was determined by measuring the OD value.

TABLE 5

| Strain to be tested | C(αC + Y + X) | Colony count (d5) × 10exp(7) | OD 660 nm (d5) |
|---|---|---|---|
| *E. coli* K12 NBRC3301 | Glc (2) + none | 37 | |
|  | Glc (2) + CaSi(10) | 240 | |
|  | Lac (2) + none | 74 | |
|  | Lac (2) + CaSi(10) | 200 | |
|  | Lac (2) + none |  | 1.29 |
|  | Lac (2) + BB (10) |  | 1.59 |
| *B. subtilis* NBRC13169 | Lac (2) + none | 32 | |
|  | Lac (2) + CaSi(10) | 186 | |
| *B. subtilis* NBRC13719 | Glc(1) + Yex (0.5) + none + |  | 1.23 |
|  | (EtO)Me2Si + |  | 6.69 |
|  | CaSi |  | 3.67 |
| *C. glutamicum* NBRC12168 | Glc (2) + none | 115 | |
|  | Glc (2) + CaSi(10) | 525 | |

(Results)

The results are shown in Table 5. The colony count and the OD value of *E. coli* K12 in a medium supplemented with CaSi or BB as a C source substitute compound increased than the same of *E. coli* K12 in comparison with that in a medium supplemented with only a limited amount of the C source. A similar tendency was observed with strains of the genus *Bacillus* or the genus *Corynebacterium*.

Example 4

The results of measuring the Si contents in cells of 3 strains (bacteria and fungi) that grew using Si compounds were analyzed. The results are shown herein.

Strains used: Washed cells of the following 3 strains were used.

*E. coli* K12 NBRC 3301,

*B. subtilis* Marburg NBRC13719,

*S. cerevisiae* NBRC0268.

Medium: A medium supplemented with a C source substitute compound (C (αC+X)Y) was used, where Y indicates a yeast extract (1 mg/mL) added.

Limited amount of C source: αC=lactate Na (denoted as "lac" in Figures. (1 or 3 mg/mL)). As C source substitute compounds, emSi (diethoxydimethylsilane) and mmSi (methyltrimethoxysilane) were used.

Strains to be used herein were subjected to seed culture in GY medium in a manner similar to that in Example 1. Cells were collected by centrifugation, suspended in a phosphate buffered washing solution, and then washed twice by centrifugation. The suspension of thus washed cells was used to seed at 5% (v/v) into a medium. Medium of 120 mL was added to a 500-mL square flask (Nalgene). Flasks were shaken and then cultured at 35° C. and 130 rpm. After 22 hours, the culture was finished, and OD and pH were measured.

Cells were collected by centrifugation from about 100 mL of the culture fluid, and then washed 3 times by centrifugation in a phosphate buffered washing solution. 3 mL of acetone was added to the precipitate, the resultant was stirred, and then it was stored in a cold place overnight (for one day and one night). This was repeated once again.

After the 2nd treatment with acetone, acetone was removed by air drying and then by keeping stand at 30° C. for drying. Thus, acetone-treated dried cells were obtained.

The content of the Si element in acetone-treated cells was measured by ICP/MS (Inductively Combined Plasma Ion Trapping Mass Spectrometry). According to a conventional method for ICP/MS, cells were heated in nitric acid for degradation, and then filled up with water to a presice volume of 15 mL. The solution was used as the material to be subjected to measurement by ICP/MS. The Si content (ng) per mg (weight) of acetone-treated cells was calculated from the thus obtained result.

TABLE 6

| Strain | Medium ingredient | D 1 OD 660 nm | D 1pH | D1ACW mg/100 mL | Si content (ng/mg) in acetone cell |
|---|---|---|---|---|---|
| 1 E. coli K12 | lac 1 + emSi 5 | 1.79 | 6.47 | 203 | 96 |
| 2 B. subtilis Marburg | lac 3 + Glc 5 | 3.48 | 5.36 | 796 | 74 |
| 3 B. subtilis Marburg | lac 1 + emSi 5 | 2.48 | 6.6 | 289 | 126 |
| 4 B. subtilis Marburg | lac 3 + mmSi 5 | 2 | 6.66 | 309 | 126 |
| 5 S. cerevisiae | lac 3 + Glc 5 | 5.55 | 5.95 | 739 | 56 |
| 6 S. cerevisiae | lac 3 + mmSi 5 | 3.14 | 6.73 | 274 | 142 |

The results are shown in Table 6. The Si content in acetone-treated cells of *B. subtilis* grown in the presence of the Si compound under the conditions of the present invention was found to be 120 ppm or higher (test Nos. 3 and 4). On the other hand, the Si content in control cells (test No. 2) grown with glucose was 80 ppm or lower. The similar tendency was observed for yeast *S. cerevisiae*.

Example 5

Figure 3:
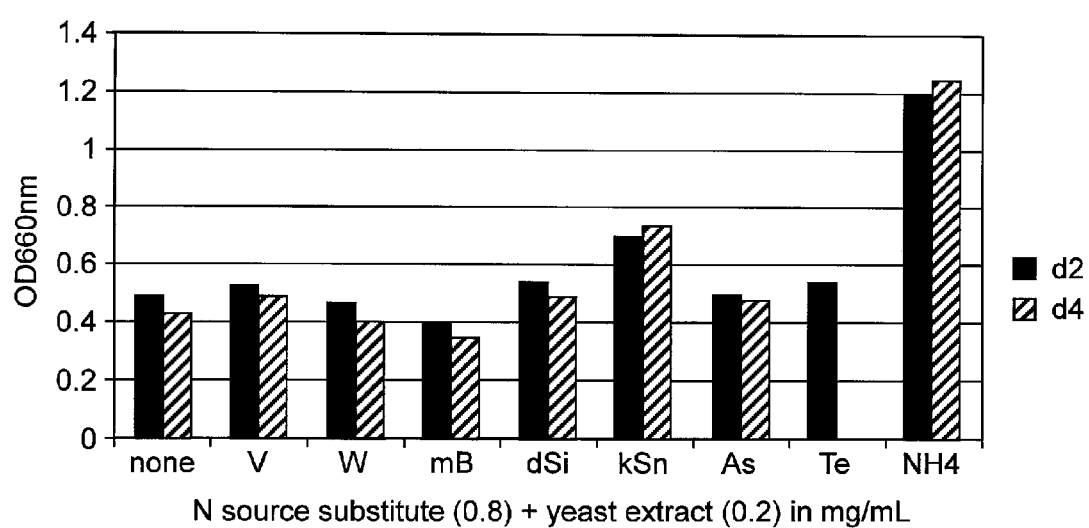
FIG. 3 shows the results of examining the growth of *Escherichia coli* (washed cells) in an N source-deficient medium N (−) supplemented with a limited amount of an N source (denoted as "αN") and an N source substitute compound (denoted as "X").

*Escherichia coli* (washed cells) growth in a medium supplemented with an N source substitute compound (that is, N (αN+X) medium) prepared by adding a limited amount of an N source (denoted as "αN") and the N source substitute compound (denoted as "X") to an N source-deleted medium N (−)) was examined.
(Method)
Washed cells of *E. coli* K12 NBRC3301 were used as starter cells.
Medium: N (αN+X)Yk medium was used in growth test. Herein, the following substances were added to an N source-deficient N(−) medium. A limited amount of yeast extract (Y) (0.2 mg/mL) as an N source (αN), the N source substitute compound(X) (0.8 mg/mL), and 2 ketoglutaric acid (k) (0.1 mg/mL) were added.
Culture conditions: Cells were cultured in 10 mL/TT, 35° C., and 130 rpm. The OD value on day 2 (d2) and on day 4 (d4) were measured. However, a black precipitate was generated on day 4 in a culture fluid with Te (sodium tellurate) so that OD could not be measured.
(Results)
The results are shown in FIG. 3. The amount (OD value) of the growth of *E. coli* K12 increased when a compound containing Si or the like had been added as N source substitute compound in the presence of a limited amount of N source, compared with the control to which no N substitute compound was added. However, the degree of the increase was small.

Example 6

Figure 4:
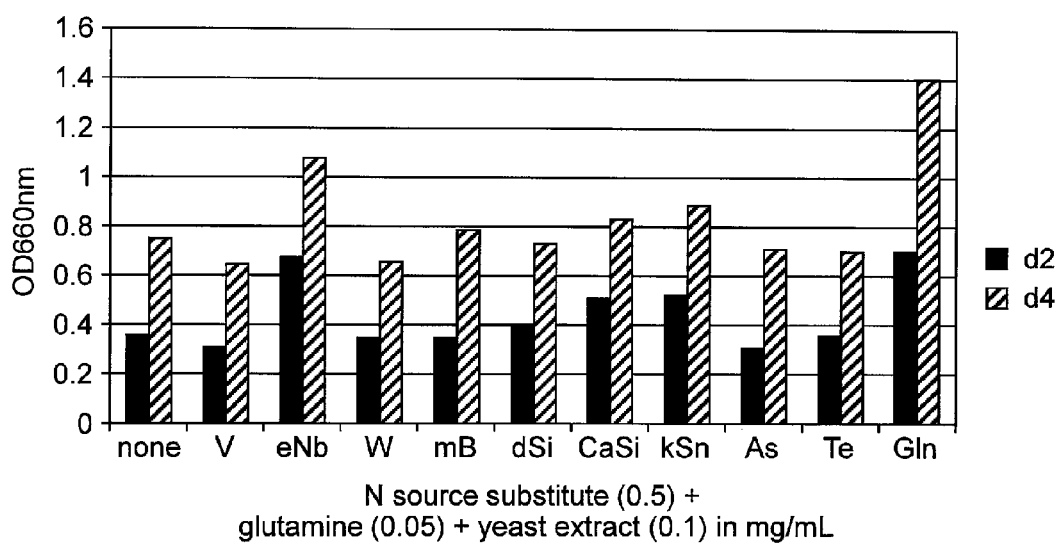
FIG. 4 shows the results of examining the growth of *Escherichia coli* (starved culture cells) in a medium containing a limited amount of an N source (denoted as "αN") and an N source substitute compound (denoted as "X").

In a manner similar to that in Example 5, growth of *Escherichia coli* (N source starved cells) in media containing limited amounts of N sources (denoted as "αN") and N source substitute compounds (denoted as "X") was examined.
(Method)
*E. coli* K12 NBRC3301 was used. N source starved cells were used as starter cells.
An N source-deleted medium (N(−) medium) was used for N source starvation culture. N(αN+X)Yk medium was used for a growth test. As limited amounts of the N sources (αN), glutamine (0.05 mg/mL), yeast extract (Y) (0.1 mg/mL), and 2ketoglutaric acid (κ) (0.1 mg/mL) were used.
Culture conditions: Cells were cultured in 10 mL/TT, 35° C., and 130 rpm. The OD value on day 2 (d2) and the same on day 4 (d4) were measured.
(Results)
The results are shown in FIG. 4. *E. coli* K12 growth (OD value) increased when an organic or inorganic compound containing Nb, B, Si, or Sn as an N source substitute compound had been added in the presence of a limited amount of N source compared with the control to which no N substitute compound was added. The types of N source substitute compound and growth increase tended to be noticed more than that in Example 5.

Example 7

Figure 5:
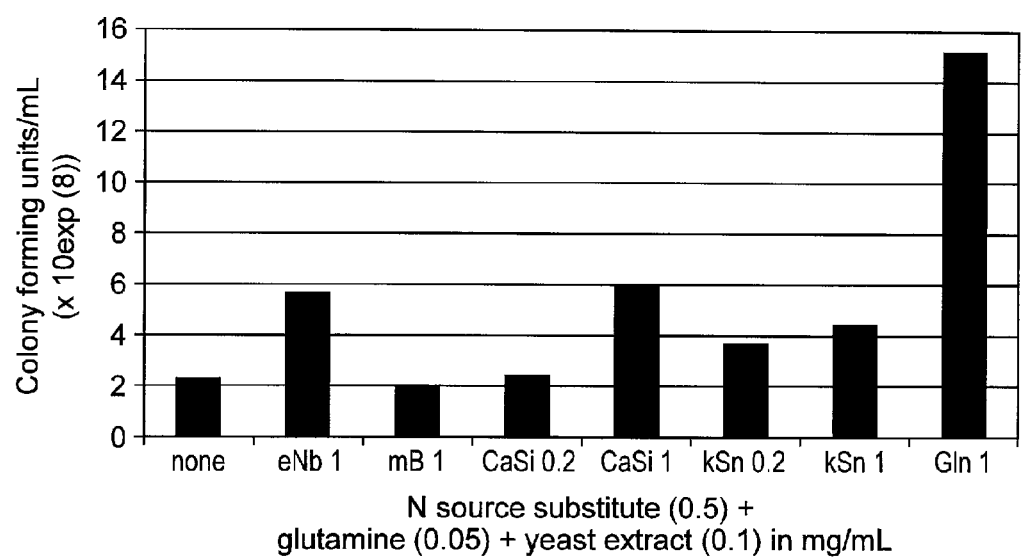
FIG. 5 shows the results of culturing the *E. coli* K12 NBRC3301 strain and then measuring the colony forming units by a colony counting method.

In a manner similar to that in Example 6, *E. coli* K12 NBRC3301 was cultured. The amount of growth was measured by a colony counting method.
(Method)
Cultivation was conducted in a manner similar to that in Example 6. Some of N source substitute compounds were water-insoluble. Measurement was also carried out by colony counting method that could give most reliable results under the conditions employed. The colony counting method was conducted by seeding with 10-fold serial dilutions of culture fluid on GY agar medium, incubated at 35° C. for 2 days, and then counting the number of colonies.
(Results)
The results are shown in FIG. 5. *Escherichia coli* colony counts increased when an organic or inorganic compound containing niobium, silicon, tin, or the like were added to medium as N source substitute compound compared the control culture to which no N source substitute compound was added. Furthermore, *Escherichia coli* growth increased in a dose-dependent manner when a silicon or tin compound had been added as an N source substitute compound.

Example 8

In a manner similar to that in Example 6, *B. subtilis* Marburg NBRC13719 was cultured. N source starved culture cells were used as starter cells.

(Results)

Figure 6:
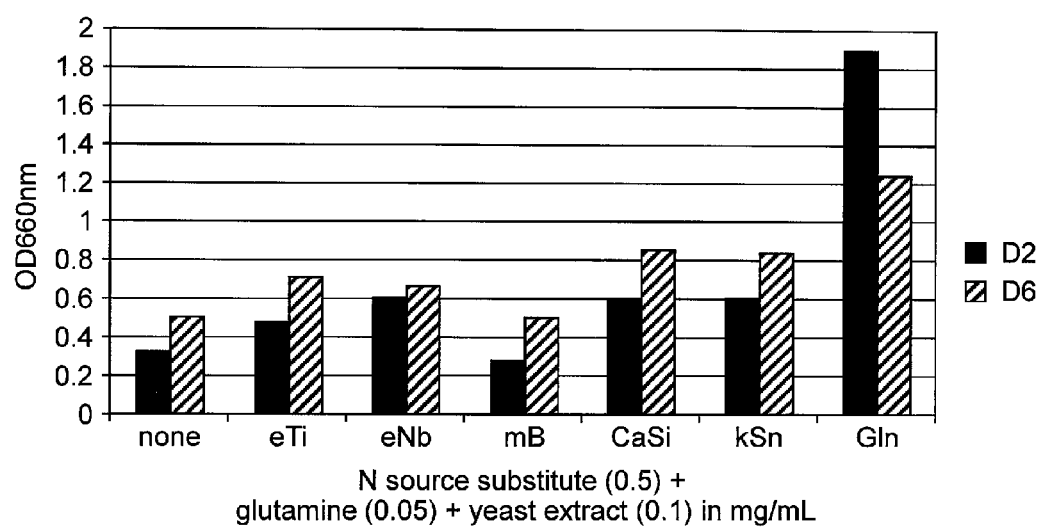
FIG. 6 shows the results of examining the growth of N-starved culture cells of the *B. subtilis* Marburg NBRC13719 strain as starter cells.

The OD values on day 2 of culture (D2) and on day 6 of culture (D6) are shown in FIG. 6. The growth of the *B. subtilis* Marburg strain increased when an organic or inorganic compound containing Ti, Nb, Si, Sn, or the like was added as an N source substitute compound, compared with the control culture to which no N substitute was added.

Example 9

*Escherichia coli* growth in a medium supplemented with a P source substitute compound (that is, the P (αP+X) medium) prepared by adding a limited amount of a P source (denoted as "αP") and a P source substitute compound (denoted as "X") to a P source-deleted medium (P(−) medium) was examined.

(Method)

*E. coli* K12 NBRC3301 was used. P source starved culture cells were used as starter cells.

Medium: P source-deleted medium (P(−) medium) was used for P source starvation culture. P (αP+X)AA medium prepared by adding αP+X to a P(−) medium was used for a growth test. Here, a limited amount of $KH_2PO_4$ (0.002 mg/mL) as the P source (αP) and a compound (0.5 mg/mL) as a P source substitute compound (X) as shown in Figures were added to the medium and then cells were cultured. Moreover, a mixture of 20 kind of amino acid (AA, 2.8 mg/mL) and a buffering agent, glutamate Na (8 mg/mL), were added to the media used for growth test.

Culture Conditions: 10 mL/TT, 33° C., 160 rpm

Microorganisms to be used herein were subjected to seed culture, starvation culture following thereto, growth test culture, and the like as described below.

Starter cells were cultured in GY medium at 33° C. overnight (for one day and one night), and then collected by centrifugation. Cells were washed twice by centrifugation in a glutamate buffered washing solution. While the concentration of the cells was adjusted to OD at 660 nm of about 5, washed cells were suspended again in a P(−) medium. The resultant was shaken at 30° C. (that is, in P source starvation culture conditions). The suspension with OD of about 5 was used to seed at 5-7% (v/v) to a medium to be used herein, followed by shaking at 33° C. and 140 rpm. Small quantity of the culture fluid was withdrawn on day 2 of culture (d2) and day 3 (d3) and then diluted 10-fold with water. The OD of the diluent was measured at 660 nm, to give growth amount.

(Results)

Figure 7:
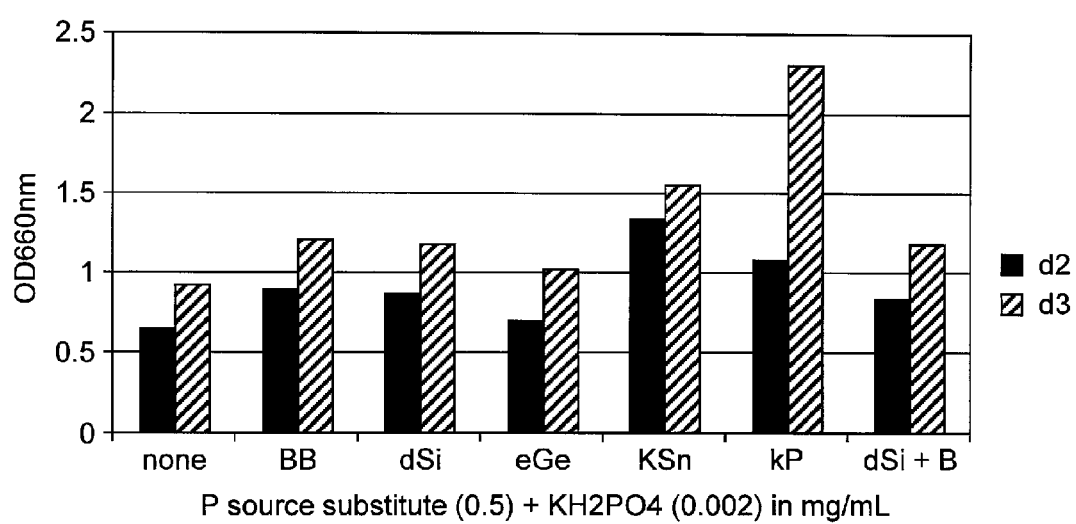
FIG. 7 shows the results of examining the growth of *Escherichia coli* NBRC3301 in a P source-deleted medium supplemented with a limited amount of a P source (denoted as "αP") and a P source substitute compound (denoted as "X").

The results are shown in FIG. 7. When P source starved culture cells of *E. coli* K12 was used, the amount of growth (OD value) increased when a compound containing B, Si, Ge, Sn, or the like as a P source substitute compound was added in the presence of a limited amount of a P source, compared with control culture to which no P substitute compound was added. When washed cells of *E. coli* K12 grown in GY medium was used for comparison, the types of P source substitute compound and the growth tended to be at lower levels.

Example 10

In a manner similar to that in Example 9, *Nocardia asteroides* growth was examined in a medium supplemented with a limited amount of P source (denoted as "αP") and a P source substitute compound (denoted as "X").

(Method)

*Nocardia asteroids* NBRC15531 was used. Washed cells were used as starter cells. Medium: A medium supplemented with a P source substitute compound (P (αP+X)AA medium) was used for a growth test. Here, a limited amount of $KH_2PO_4$ (0.02 mg/mL) was used as a P source (αP) and a compound (0.3 mg/mL) shown in Figures was used as a P source substitute compound (X). A mixture of 20 kind of amino acid (AA, 4.5 mg/mL) and Good's buffering agent MOPS (10.5 mg/mL) were added to a growth test medium. Tween 20 (0.1 mg/mL) was added to all media and washing solutions.

Culture conditions: 10 mL/TT, 35° C., 140 rpm

Strains used herein were subjected to seed culture, growth test, and the like as described below.

Starter cells were cultured in GY medium at 33° C. for 2 days and then collected by centrifugation. Cells were washed twice by centrifugation in a MOPS buffered washing solution. The suspension with the OD of 5 was then used to seed at 5-7% (v/v) to a medium to be used herein, followed by culture with shaking at 33° C. and 140 rpm. A small quantity of the culture fluid was withdrawn on day 4 of culture (d4) and then diluted 10 fold with water. The OD of the diluent was measured at 660 nm to give the amount of growth.

(Results)

Figure 8:
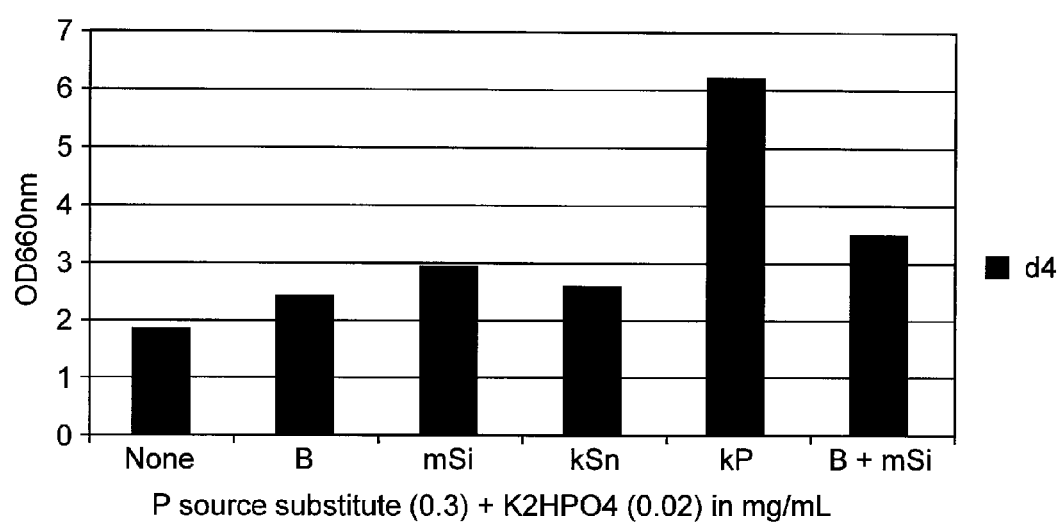
FIG. 8 shows the results of examining the growth of *Nocardia asteroides* NBRC15531 in a medium supplemented in a manner similar to the above with a limited amount of a P source (denoted as "αP") and a P source substitute compound (denoted as "X").

The results are shown in FIG. 8. The amount of the growth (OD value) of *Nocardia asteroides* increased when a compound containing B, Si, Sn, or the like was added as P source substitute compound in the presence of a limited amount of a P source, than that of the control to which no P substitute compound was added.

Example 11

In a manner similar to that in Example 10, *Nocardia asteroides* growth was examined in time lapse manner.

(Results)

Figure 9:
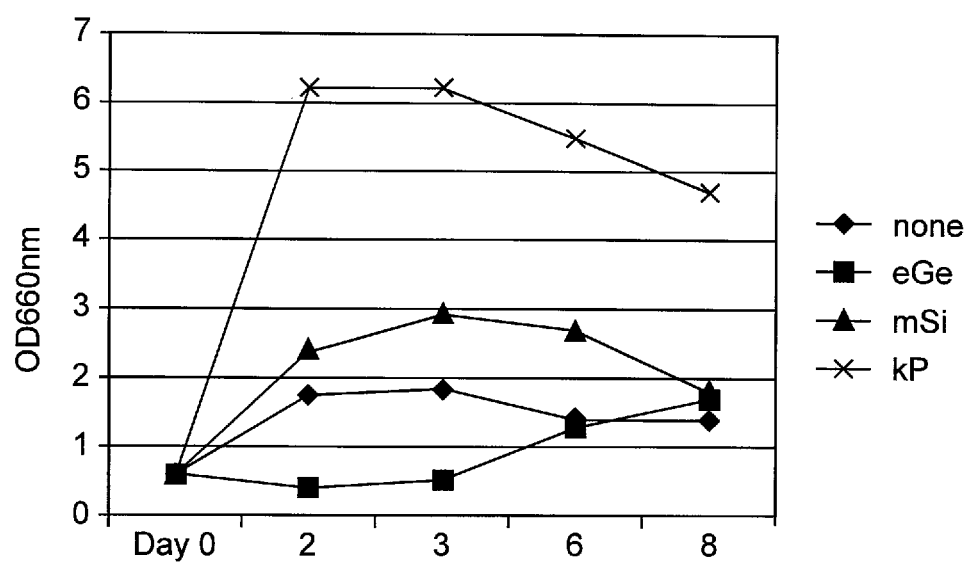
FIG. 9 shows the results of examining the time lapse growth of *Nocardia asteroides* NBRC15531 in a manner similar to the above.

The results are shown in FIG. 9. The amount of growth (OD value) of a strain of *Nocardia asteroides* also increased when a Ge-containing compound was added as a P source substitute compound other than an Si compound in the presence of a limited amount of P source.

Example 12

*Escherichia coli* growth was examined in an S(αS+X)Yfa medium prepared by adding a limited amount of S source (denoted as "αS") and an S source substitute compound (denoted as "X") to an S source-deleted medium S (−).

(Method)

*E. coli* K12 NBRC3301 was used. Washed cells thereof were used as starter cells.

Medium: S(αS+X)Yfa medium that had been specifically prepared by adding a limited amount of an S source (αS) and an S source substitute compound (X) to S source-deleted medium (S (−)) was used for a growth test. Here, $Na_2SO_4$ (0.01 mg/mL) as a limited amount of an S source (αS), a compound as an S source substitute compound (X) (0.2 mg/mL) shown in Figures, and furthermore, (Y) yeast extract (0.1), (f) oleic acid Na (0.1), (a) a mixture (4.8 mg/mL) of 18 kind of amino acid excluding methionine and cysteine (sulfur-containing amino acids), and glutamic acid Na (6 mg/mL) as a buffering agent were added.

Culture Conditions: 10 mL/TT, 35° C., 130 rpm

Microorganism used herein were subjected to seed culture and growth test, and others, as described below.

Starter cells were cultured in GY medium at 33° C. overnight (for one day and one night) and then collected by centrifugation. Cells were washed twice by centrifugation in a Na glutamate buffered washing solution. Then a suspension was prepared so that the OD was around 5. The suspension was used to seed at 5-7% (v/v) to a medium to be used herein, followed by shaking culture at 33° C. and 140 rpm. A small quantity of the resultant was collected on day 1 (d1) and on day 3 (d3) of culture, and then diluted 10-fold with water. The OD thereof was measured at 660 nm so as to find the amount of growth.

(Results)

Figure 10:
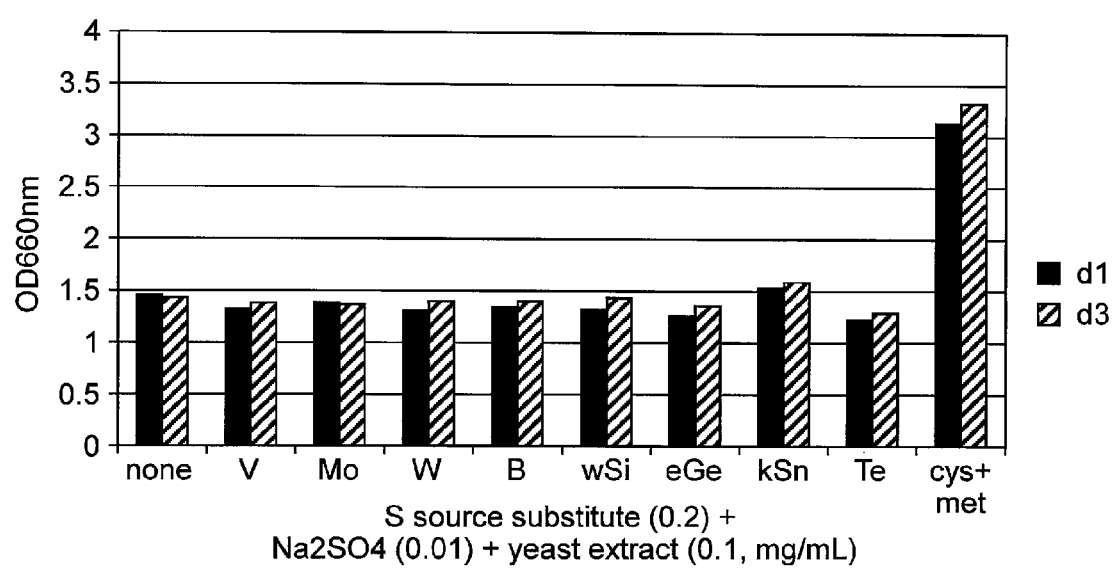
FIG. 10 shows the results of examining the growth of *Escherichia coli* NBRC3301 in an S-source deleted medium S (−) supplemented with a limited amount of an S source (denoted as "αS") and an S source substitute compound (denoted as "X").

The results are shown in FIG. 10. The growth of *E. coli* K12 in the presence of the S source substitute compound used herein was almost the same as that in the control to which no S source substitute was added substitute compound.

Example 13

An S metabolism-deficient *Escherichia coli* mutant was used in an S(αS+X)fa medium prepared by adding a limited amount of an S source (αS) and an S source substitute compound (denoted as "X") to S source-deleted medium (S(−)) in a manner similar to that in Example 12, and the growth thereof was examined.

(Method)

*E. coli* K12 NBRC3993 (met-) was used. As shown in a test example (Table 4), it was confirmed that the strain actively grew in a medium supplemented with both L-cysteine and L-methionine (0.2 mg/mL or more in total). Washed cells thereof were used as starter cells.

Medium: In accordance with the case in Example 12, an S(αS+X)fa medium was used for a growth test. Specifically, a medium prepared by adding a limited amount of an S source (αS) and an S source substitute compound (X) to an S source-deleted medium (S (−)) was used. Here, a limited amount of the S source (αS) (both L-cysteine and L-methionine (0.01 mg/mL in total)), and an S source substitute compound (X) (0.2 mg/mL) indicated in FIG. 11, and furthermore, similarly to the case in Example 12, (Y) yeast extract (0.1), (f) oleic acid Na (0.1), (a) a mixture (4.8 mg/mL) of 18 kind of amino acid excluding sulfur-containing amino acids, and glutamic acid Na (6 mg/mL) as a buffering agent were added.

Culture Conditions: 10 mL/TT, 35° C., 130 rpm.

Test microorganism was cultured in a manner similar to that in Example 12. The OD was measured every day and the OD on day 2 (d2) and the OD on day 3 (d3) are shown.

(Results)

Figure 11:
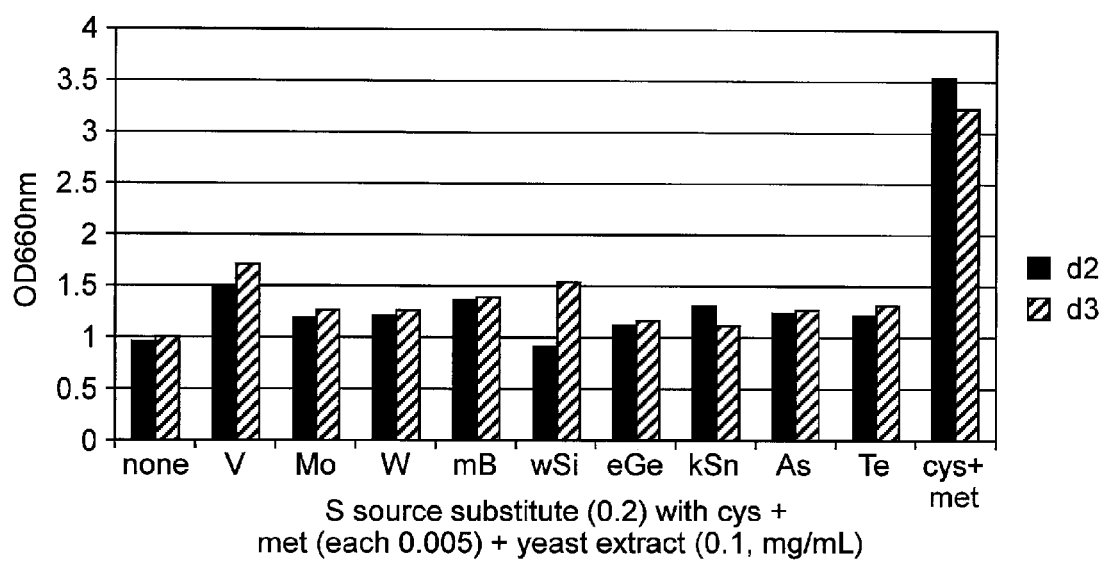
FIG. 11 shows the results of culturing *Escherichia coli* mutant strain (NBRC3993) blocked in metabolism of S and then examining the growth thereof in a manner similar to that of FIG. 10 in a S source-deleted medium S (−) supplemented with a limited amount of an S source (αS) and an S source substitute compound (denoted as "X").

The results are shown in FIG. 11.

The amount of the growth (OD value) of an *E. coli* K12-derived NBRC 3993 mutant strain requiring sulfur-containing amino acid(s) increased when a compound composed of V, Mo, W. B, Si, Ge, Sn, As, Te, etc was added as an S source substitute compound in the presence of a limited amount of S source, compared with the control to which no S source substitute was added. This result is in marked contrast to the result in Example 12 in which the parent strain was used. NBRC3993 is deficient in S metabolism because of mutation. Moreover, the amount of sulfur-containing amino acid(s) to be supplied into a medium was limited, so that the S content within cells was decreased. The result obtained here is believed to be due to facilitated incorporation of various compounds containing no element S, which was produced under such circumstances above.

Example 14

The results of testing with the use of other S source substitute compounds than those used in the test in Example 13 (FIG. 11), carried out using the *Escherichia coli* mutant strain, are described.

(Method)

The growth test was carried out in a manner similar to that in Example 13, that is, using the same strain and test media except that the amount of yeast extract added was 0.005 mg/mL. The results on day 1 (d1) and on day 2 of culture (d2) are shown.

(Results)

Figure 12:
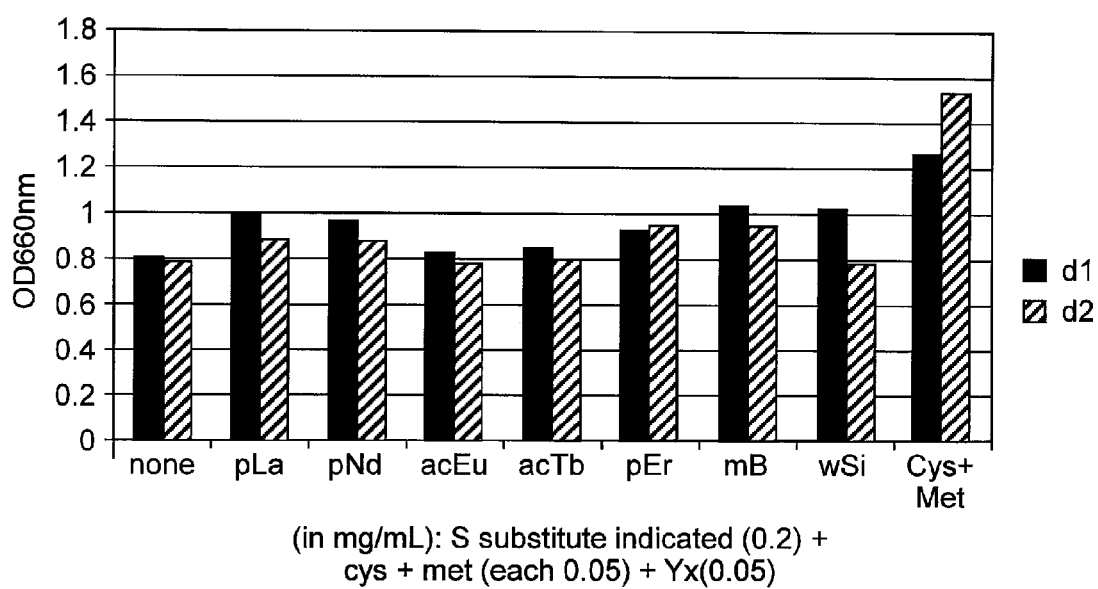
FIG. 12 shows the result of conducting a test using another S source substitute compound that was not used in the test of FIG. 11 using the NBRC3993 mutant *Escherichia coli* strain.

The results are shown in FIG. 12.

The amount of the growth (OD value) of *E. coli* NBRC 3993 mutant increased when a compound containing an element such as La, Nd, or Er as an S source substitute compound had been added in the presence of a limited amount of an S source, compared with that of the control to which no S substitute had been added. B, Si-containing compounds used as positive controls on the basis of the results in Example 13 accelerated the growth as expected.

Example 15

The relationship between the dose of Si and growth on Si of *E. coli* K12 cys-/met-mutant was examined.

(Method)

*E. coli* K12 NBRC3301 and *E. coli* K12 NBRC3993 (met-) were used.

Medium: In accordance with the case in Example 13, an S (αS+X)fa medium; that is, S source-deleted medium (S(−)) supplemented with a limited amount of S source (αS), an S source substitute compound, oleic acid (abbreviated as "f") and amino acid (denoted as "a") was used for growth test. In the case of *E. coli* K12 NBRC3301 (parent strain), $Na_2SO_4$ (0.01 mg/mL) was added as a limited amount of S source (αS). In the case of *E. coli* K12 NBRC3993 mutant, both L-cysteine and L-methionine (0.02 mg/mL in total) were added as a limited amount of S source (αS). Furthermore, sodium silicate was added as an S source substitute compound at varying concentrations.

Culture Conditions: 20 mL/Erlenmeyer flask, 35° C., 130 rpm.

(Results)

Figure 13:
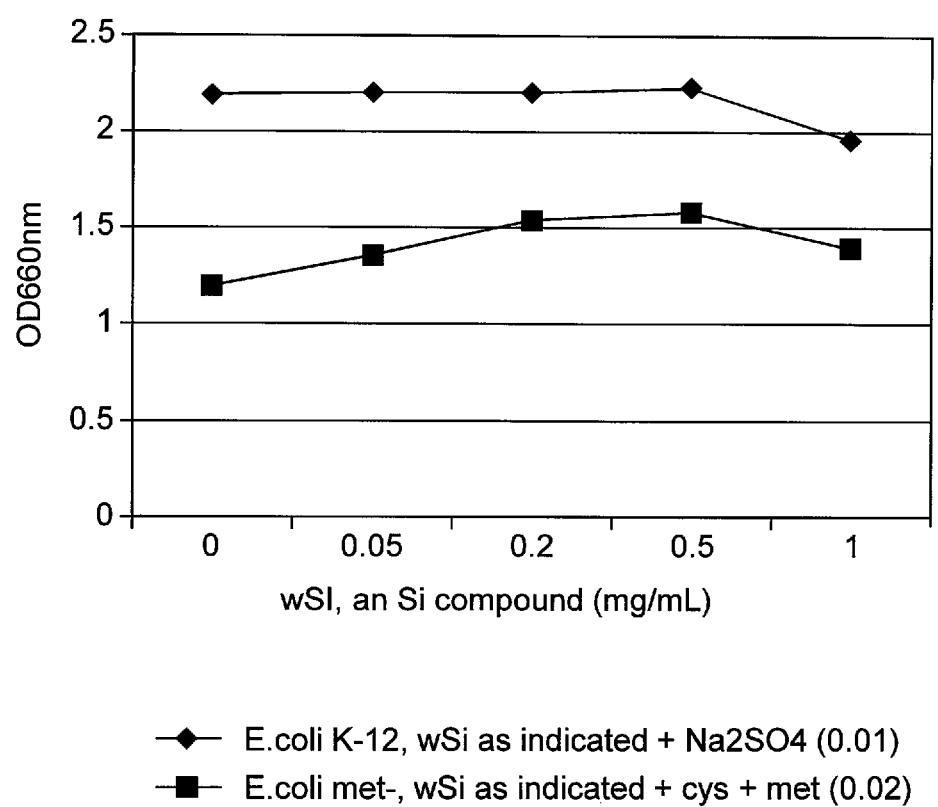
FIG. 13 shows the results of examining the relationship between the dose of Si and growth when a mutant of *E. coli* K12 strain requiring cys and met (NBRC3993) grew using Si.

The results on day 2 of culture are shown in FIG. 13. The amount of the growth of *E. coli* K12 NBRC3301 (parent strain) did not depend on the dose of sodium silicate. On the other hand, the amount of growth of *E. coli* K12 NBRC3993 (met-) mutant depended on the dose of sodium silicate. The results suggest that *E. coli* K12 NBRC3993 (met-) mutant incorporated silicic acid as an essential compound and then grew under the conditions employed herein. The results are in positive agreement with the results of Examples 12, 13, and 14.

Example 16

*Escherichia coli* (parent strain) was subjected to S source starvation culture for a period of one subculture, and to subculture 5 times for adaptation. Then, the strain was grown in the presence of a limited amount of S source and an inorganic silicon compound. The resulting cells were subjected to elementary analysis to give cellular silicon contents.

(Method)

Strain used: *E. coli* K12NBRC3301 was used. S source starved culture cells were used as starter cells.

Medium: An S source-deleted medium (S(−)fa medium) was used for S source starvation culture. An S(dSi)fa medium with sodium disilicate (abbreviated as "dSi." See Table 2 and Table 3) used therein as an S source substitute compound was used for adaptation culture. An S source substitute compound supplemented medium (S(αS+dSi)fa medium) prepared by adding a limited amount of S source (αS) and a silicon compound to S(−)fa medium was used for a growth test. Here, sodium sulfate (0 or 0.02) (in mg/mL) as a limited amount of S source (αS), sodium disilicate (dSi, 0.4) as S source substitute compound, and in addition, oleic acid Na (0.1), a mixture (4.8) of 18 kind of amino acid excluding methionine and cysteine (sulfur-containing amino acids), and glutamic acid Na (8) as buffering agent were added.

(Culture Method)
Culture and analysis were carried out as described below.

1. S Source Starvation Culture and Adaptation Culture

*E. coli* K12 NBRC3301 was subjected to seed culture in GY medium. Then cells were transferred to an S(−)fa medium for S source starvation culture. Next, S-starved culture cells were suspended in an S (dSi)fa medium in which were not supplemented with S source, but supplemented with dSi as a silicon compound, and then subjected to adaptation culture in an S(dSi)fa medium (20 mL) in a 100-mL Erlenmeyer flask at 35° C. The subculture was repeated 5 times in the adaptation culture. Finally, cells were collected by centrifugation and then stored in a cold place.

2. Culture for Production of Cells

Next, cells stored after adaptation culture were subjected to seed culture for a period of 2 passages in an S(dSi)fa medium. The cells were seeded in 120 mL of an S(αS+dSi)fa medium in a 500-mL plastic square flask at 35° C. for 2 to 4 days.

After finishing of the culture, cells were collected by centrifugation, washed with a sodium glutamate buffer, and then concentrated to about 10 mL. The concentrate was kept at 60-65° C. for 30 minutes so as to inactivate *Escherichia coli* cells. The resultant was stored in a cool place.

3. Elementary Analysis of Cells

Elementary analysis was conducted for cells by the ICP-MS method (Inductively Combined Plasma Ion Trapping Mass Spectrometry). Each sample of cells was subjected to decomposition with nitric acid, and then adjusted to a constant volume of 60 mL. Portions thereof were applied to instruments for elementary analysis. After analysis, each result was shown with conversion into the concentration in the original culture fluid.

(Results)

First, as a result of adaptation culture in S(dSi)fa medium, the OD values of the 1st to the 5th subculture at the end of each culture are as follows. Each result is a mean value of the OD values of 2 to 3 culture flasks. The OD value at the initiation of culture ranged from 0.4 to 0.5.

(Days for culture, OD 660 nm) (1) d 13, OD 2.13, (2) d 9, OD 2.00, (3) d 7, OD 1.91, (4) d 3, OD 1.93, (5) d 3, OD 3.22.

Next, Table 7 shows the growth after culturing in the presence of a limited amount of S source and sodium disilicate (dSi), and the result of measuring the silicon content. The S content was found to be 49-67 mcg (microgram, the same applies to the following)/mL in the positive controls of test #1 and test #2. In test No. #3, because of the limited amount of the S source in the medium, the S content decreased to 9.6 mcg/mL. On the other hand, the silicon content was low in #1 and #2, but increased 50-100 times in #3 and #4 wherein *E. coli* grew in the presence of silicon. Changes in phosphoric acid content were gentle.

The results suggest that when the culture method of the present patent application is employed, the S content can be decreased and at the same time the silicon content can be increased within the cells of *Escherichia coli* K12.

TABLE 7

| Test No. medium | Additive (mg/mL) | Days of culture (pH) | Culture fluid volume (mL)(OD 660 nm) | S content (mg/L) | Si content (mg/L) | P content (mg/L) |
| --- | --- | --- | --- | --- | --- | --- |
| 1. GY | None | d2 (pH 5.17) | 170 (OD 6.0) | 49 | 1.3 | 200 |
| 2. S (−)fa | Na2SO4 (0.2) | d3 (pH 6.07) | 200 (OD 4.2) | 67 | 1.3 | 238 |
| 3. S (−)fa | Na2SO4 (0.02) + dSi (0.4) | d3 (pH 6.78) | 170 (OD 6.0) | 40 | 220 | 190 |
| 4. S (−)fa | dSi (0.4) | d4 (pH 4.83) | 190 (OD 3.0) | 9.6 | 74 | 250 |

Example 17

The result of adaptation culture of a *Nocardia* strain is as described below.

A strain of the genus *Nocardia* was grown in an S source-deleted medium (S (−) medium) supplemented with a limited amount of an S source (αS) and an S source substitute compound (X). Subsequently, cells were subcultured in a medium of the same composition so as to continue adaptation culture.

(Method)

The strain used herein was *N. asteroides* NBRC15531. After seed culture, cells were suspended in an S(−)fa medium for S-starvation culture. The resulting cells were used as starter cells.

Medium and culture conditions: Seed culture media, growth media, and the like were each supplemented with tween20 surfactant (0.1 mg/mL). The other conditions were the same as those in Example 13. The *Nocardia* strain was cultured with shaking. After the culture, adaptation culture was repeated 3 times, in which cells were subcultured in a medium of the same composition. The result of growth on day 6 (T1d6) of the 1st adaptation culture, on day 6 (T2d6) of the 2nd adaptation culture, and on day 8 (T3d8) of the 3rd adaptation culture were shown. Here, in the case of "none" and in the case of "S," measurement on the 2nd and the 3rd adaptation culture were not carried out.

(Results)

Figure 14:
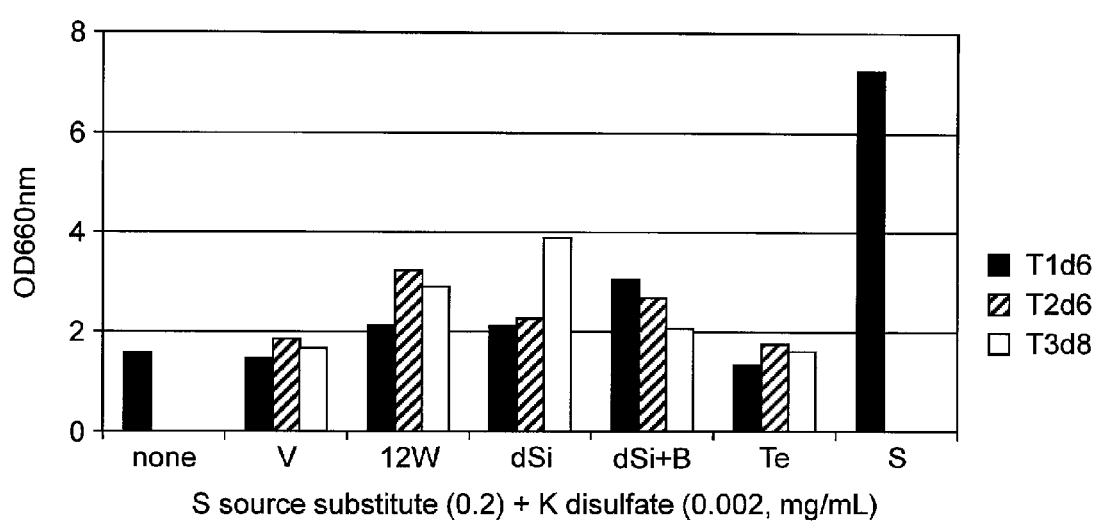
FIG. 14 shows the results of adaptation culture of *Nocardia asteroides* NBRC15531.

The results are shown in FIG. 14. The OD value of a strain of N asteroides NBRC15531 increased when a compound containing W, Si, or others as an S source substitute compound had been added, compared with the control to which no S substitute was added. The OD value tended to be higher in the 3rd subculture than that in the 1st subculture. The results also indicate that even if there is a slight difference in OD value between the 1st subculture and the control (to which no Si compound had been added), the difference in OD value between the 2nd subculturen (or later) and the control can become larger than the aforementioned difference.

Example 18

The growth of yeast was examined when the yeast was grown in an S source-deleted medium (S (−) medium)supplemented with a limited amount of an S source (αS) and an S source substitute compound (X), and then repeatedly subcultured in a medium of the same composition.

(Method)

The strain used herein was R pastoris NBRC10777. Washed cells were used as starter cells. This strain requires biotin. Hence, biotin was added to GY medium for seed culture and to test culture media.

Medium: An S(αS+X)bfa medium; that is, an S source-deleted medium (S(−)fa medium) supplemented with a limited amount of an S source (αS) and an S source substitute compound (X) was used for a growth test. Here, a limited amount of S source (αS) (mg/mL) (potassium disulfate (0.002)), and the S source substitute compound (X) (0.2) shown in FIG. 15, and furthermore, biotin (0.001), oleic acid Na (0.1), a mixture (4.8 mg/mL) of 18 kind of amino acid excluding methionine and cysteine (sulfur-containing amino acids), and glutamic acid Na (8 mg/mL) as a buffering agent were added.

Culture Conditions: 100 mL/500 mL-square flask, 27° C., 130 rpm (Results)

Figure 15:
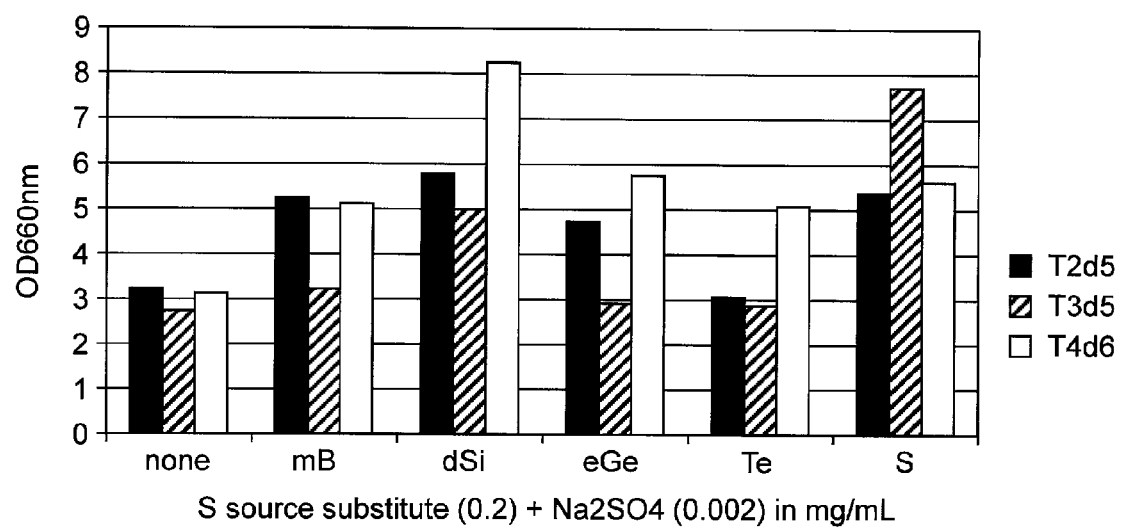
FIG. 15 shows the results of a study of yeast growth with *Pichia pastoris* NBRC10777 in an S source-deleted medium (S (−) medium) supplemented with a limited amount of an S source (αS) and a S source substitute compound (X), in which the subculture thereof was repeated in a medium of the same composition.

The results are shown in FIG. 15.

Cells on day 2 of the 1st culture were washed, used as inoculum to seed to a medium of the same composition, and then subcultured for the 2nd adaptation culture. This was continued upto the 4th adaptation culture. FIG. 15 shows the results of growth on day 5 of the 2nd adaptation culture (T2d5), on day 5 of the 3rd adaptation culture (T3d5), and on day 6 of the 4th adaptation culture (T4d6). The OD value of *P. pastoris* NBRC10777 increased when a compound containing B, Si, Ge, Te, or others as an S source substitute compound was added, compared with that of the control to which no S substitutes compound was added. The OD value tended to be higher in the 4th subculture than in the 2nd subculture.

Example 19

In addition to the above Examples, it was observed in various tests conducted in the course of research of the present patent application that various non-essential elements were incorporated by the microorganisms of the present invention. On the basis of the results of both Examples and various tests, examples of non-essential elements incorporated in each microorganism by the culture method of the present invention are summarized in Table 8. In Table 8, for example, *Escherichia coli* K12 grew using various compounds containing one, two, or more non-essential elements as constitutive elements when cultured under the various conditions of the present invention, so that a total of 13 kind of element could be incorporated. It was further revealed that when the results obtained using other microorganisms are taken together, at least a total of 15 kind of element were incorporated as essential elements by 7 strains (5 types of bacterium and 2 types of yeast).

TABLE 8

Examples of elements incorporated by microorganism

| Minimal essential medium | Microorganism | La | Nd | Tb | Er | Ti | V | Nb | Mo | W | B | Si | Ge | Sn | As | Te |
|---|---|---|---|---|---|---|---|---|---|---|---|---|---|---|---|---|
| C (αC + X) | *E. coli* K12 | | | | | | | | | | 0 | 0 | | | | |
| N (αN + X) | *E. coli* K12 | | | | | | 0 | 0 | | | 0 | 0 | | 0 | | 0 |
| P (αP + X) | *E. coli* K12 | | | | | | | | | | 0 | 0 | 0 | 0 | | |
| S (αS + X) | *E. coli* K12 | 0 | 0 | 0 | 0 | | 0 | | 0 | 0 | 0 | 0 | 0 | 0 | 0 | 0 |
| Sub total | 13 elements were incorporated by 1 bacterial strain | 0 | 0 | 0 | 0 | | 0 | | 0 | 0 | 0 | 0 | 0 | 0 | 0 | 0 |
| C (αC + X) | *B. subtilis* Marburg | | | | | | | | | | 0 | | | | | |
| N (αN + X) | *B. subtilis* Marburg | | | | | 0 | | 0 | | | 0 | | 0 | | | |
| P (αP + X) | *B. subtilis* Marburg | | | | | | | | | | 0 | 0 | 0 | | | |
| Sub total | 5 elements were incorporated by 1 bacterial strain | | | | | 0 | | 0 | | | 0 | 0 | 0 | | | |
| C (αC + X) | *C. glutamicum* | | | | | | | | | | | 0 | | | | |
| P (αP + X) | *M. smegmatis* | | | | | | | | | | | 0 | 0 | | | |
| N (αN + X) | *N. asteroids* | | | | | | | | | | 0 | | 0 | | | |
| P (αP + X) | *N. asteroids* | | | | | | | | | | 0 | 0 | 0 | | | |
| S (αS + X) | *N. asteroids* | | | | | | 0 | | 0 | 0 | 0 | 0 | 0 | | | 0 |
| Sub total | 7 elements were incorporated by 3 bacterial strains | | | | | | 0 | | 0 | 0 | 0 | 0 | 0 | | | 0 |
| P (αP + X) | *P. pastoris* | | | | | | | | | | 0 | 0 | 0 | | | 0 |
| C (αC + X) | *S. cerevisiae* | | | | | | | | | | | 0 | | | | |
| S (αS + X) | *S. cerevisiae* | | | | | | | 0 | | | 0 | | | | | |
| Sub total | 5 elements were incorporated by 2 yeast strains | | | | | | | 0 | | | 0 | 0 | 0 | | | 0 |
| Total | 15 elements were incorporated by 7 strains of bacteria and yeast | La | Nd | Tb | Er | Ti | V | Nb | Mo | W | B | Si | Ge | Sn | As | Te |

The abbreviated names of microorganism used are as follows.

Bacterial Strains

E. coli: *Escherichia coli*, B. subtilis: *Bacillus subtilis*, C. glutamicum: *Corynebacterium glutamicum*, M. smegmatis: *Mycobacterium smegmatis*, N. asteroides: *Nocardia asteroides*, Yeast Strains P. pastoris: *Pichia pastoris*, S. cerevisiae: *Saccharomyces cerevisiae*

INDUSTRIAL APPLICABILITY

The present invention can be used for production of useful materials, and in a broad range of industrial fields including agriculture, foods, medicine, beauty, environment, and basic material industries.

The method for culturing microorganisms of the present invention has the following characteristics.

(1) It enables incorporation of one, two, or more non-essential elements selected from among 15 or more kind thereof, the presence of which in cells of general microorganisms has not been known, into existing microorganisms.

(2) It enables efficient incorporation of non-essential elements. When applied to *Escherichia coli* K12, 10 or more non-essential sources can be incorporated (into cells). When *Escherichia coli* was grown in a medium supplemented with an Si-containing compound, *E. coli* grew in a dose-dependent manner and incorporates Si element into the cells. This is understood to mean that Si element was incorporated as a cell constituent. Furthermore, the content of Si element in *E. coli* cells was 50 or more higher than that in control cells. The method of the present invention is applicable to other bacteria and fungi. As a result, many non-essential elements can be efficiently incorporated into bacteria and fungi.

(3) According to the present invention, existing microorganisms were successfully caused to incorporate non-essential elements that are believed to be safe or elements that are experimentally known to have low toxicity. Unlike the original strains, the thus obtained microbial cells contain new elements, and thus they are expected to have acquired new metabolic functions and new capacity for production of materials.

(4) As known microorganisms have a high degree of usefulness in production of materials, similarly, microbial cells obtained by the present invention are expected to be useful in production of pharmaceutical products, vaccine production, food production, and the like.

(5) Microbial cells obtained by the present invention are expected to be useful for development of technology for recovering or removing useful or harmful metals from the environment. The microbial cells are also useful for decomposition of substances of environmental concern.

All publications, patents, and patent applications cited herein are incorporated herein in their entirety.

The invention claimed is:

1. A method for culturing a microorganism to cause a microbial cell to incorporate a substitute element as a constitutive element thereof, comprising culturing a microorganism and letting the microorganism grow in a medium supplemented with a substitute compound that is prepared by adding a compound containing a substitute element substituting for C, N, P, or S to a nutrient-limited medium prepared by limiting a nutrition source containing C, N, P, or S in the medium, wherein the substitute compound is an inorganic or organic compound and the substitute element is at least one selected from the group consisting of elements V, Mo, B, Si and Ge, and wherein the microorganism is a strain belonging to bacteria, yeasts, or fungi.

2. The method according to claim 1, wherein the microorganism is a mutant strain having enhanced capacity for incorporating the substitute element, including a mutant strain in which the capacity for using a nutrition source containing any one of C, N, P, and S is lowered or deleted, and a mutant strain having enhanced capacity for using a substitute compound.

3. The method according to claim 1, wherein: the substitute compound is an oxide, a halide, an alkali metal salt, a complex of the substitute element, or an organic compound to which a simple alkyl group(s), alcohol, an organic acid, amine, or an amide group(s), is(are) bound.

4. The method according to claim 1, wherein the elemental composition of microbial cells, a cell constitutive substance, and/or the amount and/or property of a microbial metabolite are changed by varying the type and/or amount of a substitute compound to be added to a medium in which a microorganism is cultured.

5. The method according to claim 1, wherein the microorganism is a strain belonging to any one of the genera of *Bacillus, Corynebacterium, Mycobacterium, Nocardia, Streptomyces, Bifidobacterium, Lactobacillus, Chlamydia, Escherichia, Candida, Pichia, Saccharomyces, Aspergillus, Cephalosporium*, and *Penicillium*.

6. The method according to claim 5, wherein the microorganism is a mutant strain having enhanced capacity for incorporating the substitute element, including a mutant strain in which the capacity for using a nutrition source containing any one of C, N, P, and S is lowered or deleted, and a mutant strain having enhanced capacity for using a substitute compound.

7. The method according to claim 1, wherein the substitute element is at least one selected from the group consisting of B, Si, and Ge.

8. The method according to claim 5, wherein the substitute element is at least one selected from the group consisting of B, Si, and Ge.

9. The method according to claim 1, wherein the substitute element is Si.

10. The method according to claim 5, wherein the substitute element is Si.

11. The method according to claim 5, wherein: the substitute compound is an oxide, a halide, an alkali metal salt, a complex of the substitute element, or an organic compound to which a simple alkyl group(s), alcohol, an organic acid, amine, or an amide group(s), is(are) bound.

12. The method according to claim 1, wherein: the medium supplemented with a substitute compound is a medium prepared by adding a compound containing at least one selected from the group consisting of B, Si, and Ge to a nutrient-limited medium in which a nutrition source containing the element C, N, P, or S is limited;

and the microorganism is a strain belonging to any one of the genera selected from the group consisting of *Bacillus, Corynebacterium, Mycobacterium, Nocardia, Streptomyces, Bifidobacterium, Lactobacillus, Chlamydia, Escherichia, Candida, Pichia, Saccharomyces, Aspergillus, Cephalosporium*, and *Penicillium*.

13. The method according to claim 5, wherein the medium supplemented with a substitute compound is a medium prepared by adding a compound containing at least one selected from the group consisting of B, Si, and Ge to a nutrient-limited medium in which a nutrition source containing the element C, N, P, or S is limited.

14. The method according to claim 5, wherein the elemental composition of microbial cells, a cell constitutive substance, and/or the amount and/or property of a microbial metabolite are changed by varying the type and/or amount of a substitute compound to be added to a medium in which a microorganism is cultured.

15. A method for culturing a microorganism belonging to any one of *Escherichia coli, Bacillus subtilis, Corynebacterium glutamicum*, or *Saccharomyces cerevisiae* to cause a microbial cell to incorporate Si as a constitutive element thereof, comprising culturing a microorganism and letting the microorganism grow in a medium supplemented with a substitute compound that is prepared by adding a compound containing Si substituting for C to a C source-limited medium prepared by limiting C source in the medium, wherein the substitute compound is selected from organic Si compounds and inorganic Si compounds.

16. The method according to claim 15, wherein the substitute compound is selected from silane and alkali metal silicate salt.

17. The method according to claim 16, wherein the C source contained in a limited amount in a C source limited medium is sodium lactate, sodium glutamate or glucose, to each of which yeast extract is further added, and wherein the silane is methyltrimethoxylsilane, diethoxydimethylsilane, or tetraethyl silicate, and wherein the alkali metal salt of silicate is calcium silicate.

\* \* \* \* \*